US009526765B2

(12) United States Patent
Ponnapakkam et al.

(10) Patent No.: US 9,526,765 B2
(45) Date of Patent: Dec. 27, 2016

(54) DELIVERY OF THERAPEUTIC AGENTS BY A COLLAGEN BINDING PROTEIN

(71) Applicants: The Board of Trustees of the University of Arkansas, Little Rock, AR (US); The Kitasato Institute, Tokyo (JP); MONTEFIORE MEDICAL CENTER, New York, NY (US)

(72) Inventors: Tulasi Ponnapakkam, New York, NY (US); Sagaya Theresa Leena Philominathan, Cheshire, CT (US); Joshua Sakon, Fayetteville, AR (US); Ranjitha Katikaneni, New York, NY (US); Takaki Koide, Tokyo (JP); Osamu Matsushita, Kanagawa (JP); Robert C. Gensure, New York, NY (US)

(73) Assignees: The Kitasato Institute (JP); Montefiore Medical Center; The Board of Trustees of the University of Arkansas

( * ) Notice: Subject to any disclaimer, the term of this patent is extended or adjusted under 35 U.S.C. 154(b) by 0 days.

(21) Appl. No.: 14/378,067

(22) PCT Filed: Feb. 11, 2013

(86) PCT No.: PCT/US2013/025541
§ 371 (c)(1),
(2) Date: Aug. 11, 2014

(87) PCT Pub. No.: WO2013/120060
PCT Pub. Date: Aug. 15, 2013

(65) Prior Publication Data
US 2015/0038423 A1    Feb. 5, 2015

Related U.S. Application Data

(63) Continuation-in-part of application No. PCT/US2012/069831, filed on Dec. 14, 2012.

(60) Provisional application No. 61/596,869, filed on Feb. 9, 2012.

(51) Int. Cl.
A61K 38/10    (2006.01)
A61K 38/16    (2006.01)
A61K 39/00    (2006.01)
A61K 38/39    (2006.01)
C07K 14/635   (2006.01)
A61K 38/29    (2006.01)
A61K 47/48    (2006.01)
A61K 38/48    (2006.01)

(52) U.S. Cl.
CPC ............. A61K 38/29 (2013.01); A61K 38/48 (2013.01); A61K 47/48246 (2013.01); C12Y 304/00 (2013.01)

(58) Field of Classification Search
None
See application file for complete search history.

(56) References Cited

U.S. PATENT DOCUMENTS

| | | | |
|---|---|---|---|
| 5,914,126 A | 6/1999 | Li et al. | |
| 6,362,163 B1 | 3/2002 | Gardella et al. | |
| 8,450,273 B2 | 5/2013 | Sakon et al. | |
| 9,062,300 B2 * | 6/2015 | Gensure | A61K 38/29 |
| 2002/0102709 A1 | 8/2002 | Ishikawa et al. | |
| 2002/0164719 A1 | 11/2002 | Hall et al. | |
| 2003/0187232 A1 | 10/2003 | Hubbell et al. | |
| 2004/0053365 A1 | 3/2004 | Renner et al. | |
| 2004/0220094 A1 | 11/2004 | Skinner et al. | |
| 2005/0108562 A1 | 5/2005 | Riviere et al. | |
| 2005/0124537 A1 | 6/2005 | Kostenuik et al. | |
| 2005/0180986 A1 | 8/2005 | Rich et al. | |
| 2006/0014687 A1 | 1/2006 | Crine et al. | |
| 2006/0257376 A1 | 11/2006 | Scadden et al. | |
| 2009/0305352 A1 | 12/2009 | Dai et al. | |
| 2010/0129341 A1 * | 5/2010 | Sakon | A61K 38/29 424/94.6 |

FOREIGN PATENT DOCUMENTS

| | | |
|---|---|---|
| EP | 0207751 | 1/1987 |
| WO | WO 0006195 | 2/2000 |
| WO | WO 0049159 | 8/2000 |
| WO | WO 03/052091 | 6/2003 |
| WO | WO 2004071543 | 8/2004 |
| WO | WO 2005082941 | 9/2005 |
| WO | WO 2006072623 | 7/2006 |

(Continued)

OTHER PUBLICATIONS

Katikaneni, Int. J. Cancer: 131, E813-E821 (2012).*

(Continued)

*Primary Examiner* — Satyanarayana R Gudibande
(74) *Attorney, Agent, or Firm* — Andrus Intellectual Property Law, LLP

(57) ABSTRACT

Methods of delivering therapeutic agents by administering compositions including a bacterial collagen-binding polypeptide segment linked to the therapeutic agent to subjects in need of treatment with the therapeutic agent are provided. Methods of treating hyperparathyroidism, and hair loss using compositions comprising a collagen binding polypeptide and a PTH/PTHrP receptor agonist are provided. In addition, methods of reducing hair regrowth by administering a composition including a collagen binding polypeptide and a PTH/PTHrP receptor antagonist are provided.

12 Claims, 10 Drawing Sheets

(56) References Cited

FOREIGN PATENT DOCUMENTS

| WO | WO 2010087397 | 8/2010 |
|---|---|---|
| WO | WO 2011142425 | 11/2011 |
| WO | WO 2012157339 | 11/2012 |

OTHER PUBLICATIONS

Ponnapakkam, Calcif Tissue Int (2011) 88:511-520.*
Locklin, R.M. et al., "Mediators of the biphasic responses of bone to intermittent and continuously administered parathyroid hormone," J Cell Biochem. (2003) 89(1):180-90.
Locus BAA06251 (GI 710023), Collagenase precursor from Clostridium histolyticum, Jan. 30, 2003. This amino acid sequence is disclosed in this application as SEQ ID No. 6. The sequence of residues 901-1021 of BAA06251 corresponds to the collagen binding domain included in the fusion protein of SEQ ID No. 1.
Locus EAW68494 (GI 119588900), Parathyroid hormone isoform from *Homo sapiens*, Dec. 18, 2006. Residues 64-147 of EAW68494 correspond to the PTH of SEQ ID No. 7.
Lotinun, S. et al., "Differential effects of intermittent and continuous administration of parathyroid hormone on bone histomorphometry and gene expression," Endocrine. (2002) 17(1):29-36.
Lotinun, S. et el., "Triazolopyrimidine (trapidil), a platelet-derived growth factor antagonist, inhibits parathyroid bone disease in an animal model for chronic hyperparathyroidism," Endocrinology. (2003) 144(5):2000-7.
Lumachi, F. et al., "Lumbar spine bone mineral density changes in patients with primary hyperparathyroidism according to age and gender," Ann N Y Acad Sci. (2007) 1117:362-6. Epub Jul. 26, 2007.
Ma, Y.L. et al., "Catabolic effects of continuous human PTH (1--38) in vivo is associated with sustained stimulation of RANKL and inhibition of osteoprotegerin and gene-associated bone formation," Endocrinology (2001) 142(9):4047-54.
Machado Do Reis, L. et al., "Accentuated osteoclastic response to parathyroid hormone undermines bone mass acquisition in osteonectin-null mice," Bone (2008) 43(2)264-73. Epub Apr. 13, 2008.
Malluche, H.H. et al., "Endogenous calcitonin does not protect against hyperparathyroid bone disease in renal failure," Miner, Electrolyte Metab. (1986) 12(2):113-8.
Malluche, H.H. et al., "Osteomalacia and hyperparathyroid bone disease in patients with nephrotic syndrome," J Clin Invest. (1979) 63(3):494-500.
Malluche, H.H. et al., "Influence of the parathyroid glands on bone metabolism," Eur J Clin Invest. (2006) 36(Suppl 2):23-33.
Malluche, H.H. et al., "Effects of long-term infusion of physiologic doses of I-34 PTH on bone" Am J Physiol. (1982) 242(2):F197-201.
Masi, L. et al., "Molecular, biochemical and cellular biology of PTH anabolic action," J Endocrinol Invest. (2005) 28(8 Suppl):37-40.
Mathias, R. et al., "Renal bone disease in pediatric and young adult patients on hemodialysis to a children's hospital," J Am Soc Nephrol. (1993) 3(12):1938-46.
Matsushita, O. et al., "A study of the collagen-binding domain of a 116-kDa Clostridium histolyticum collagenase," J Biological Chem (1998) 273(6):3643-3648.
Matsushita, O. et al., "Gene duplication and multiplicity of C. Histolyticum collagenases," J. Bacteriol. (1999) 181:923-933.
Matsushita, O. et al., "Substrate recognition by the collagen-binding domain of Clostridium histolyticum class I collagenase," J of Biological Chem (2001) 276(12):8761-8770.
Matsushita, O., "Studies on the Clostridal Collagenases," Nippon Saikingaku Zasshi (1999) 54(4):753-761.
McCauley, L.K. et al., "PTH/PTHrP receptor is temporally regulated during osteoblast differentiation and is associated with collagen synthesis," J Cell Biochem (1996) 61:638-647.
McCauley, L.K. et al., "Proto-oncogene c-fos is transcriptionally regulated by parathyroid hormone (PTH) and PTH-related protein in a cyclic adenosine monophosphate-dependent manner in osteoblastic cells," Endocrinology (1997) 138(12):5427-33.
McCauley, L.K. et al., "Parathyroid hormone stimulates fra-2 expression in osteoblastic cells in vitro and in vivo," Endocrinology (2001) 142(5):1975-81.
Minisola, S. et al., "Trabecular bone mineral density in primary hyperparathyroidism: relationship to clinical presentation and biomarkers of skeletal turnover," Bone Miner. (1993) 20(2):113-23.
Minisola, S. et al., "Uneven deficits in vertebral bone density in postmenopausal patients with primary hyperparathyroidism as evaluated by posterior-anterior and lateral dual-energy absorptiometry." Osteoporos Int. (2002) 13(8):618-23.
Mitlak, B.H. et al., "Asymptomatic primary hyperparathyroidism," J Bone Miner Res. (1991) 6(Suppl 2):.S103-10; discussion S121-4.
Miyachi, Y. et al., "Long-term safety and efficacy of high-concentration (20 mug/g) tacalcitol ointment in psoriasis vulgaris," Eur J Dermatol (2002) 12(5):463-468.
Morley, P. et al., "Anabolic effects of parathyroid hormone on bone," Trends Endocrinol. Metab. (1997) 8(6):225-31.
Morley, P. et al., "Parathyroid hormone: an anabolic treatment for osteoporosis." Curr Pharm Des. (2001) 7(8):671-87.
Murray, E.J. et al., "E64d, a membrane-permeable cysteine protease inhibitor, attenuates the effects of parathyroid hormone on osteoblasts in vitro," Metabolism (1997) 46(9):1090-4.
Nasu, M. et al., "Stimulatory effects of parathyroid hormone and 1,25-dihydroxyvitamin D3 on insulin-like growth factor-binding protein-5 mRNA expression in osteoblastic UMR-106 cells: the difference between transient and continuous treatments." FEBS Lett. (1997) 409(1):63-6.
Neer, R.M. et al.,"Effect of parathyroid hormone (1-34) on fractures and bone mineral density in postmenopausal women with osteoporosis," N. Engl. J. Med. (2001) 344(19):1434-1441.
Nemeth, E.F., "Pharmacological regulation of parathyroid hormone secretion," Curr Pharm. Des. (2002) 8(23):2077-87.
Nilsson, P., "Bone disease in renal failure. Clinical and histomorphometric studies," Scand J Urol Nephrol Suppl. (1984) 84:1-68.
Nishi, N. et al., "Collagen-binding growth factors: Production and characterization of functional fusion proteins having a collagenbinding domain," PNAS (1998) 95(12):7018-7023.
O'Brien, C.A. et al., "IL-6 is not required for parathyroid hormone stimulation of RANKL expression, osteoclast formation, and bone loss in mice," Am J. Physiol Endocrinol Metab. (2005) 289(5):E784-93. Epub Jun. 14, 2005.
Okazaki, R., "Parathyroid hormone—its mechanisms of action and issues on clinical application," Clin Calcium. (2005) 15(5):845-51.
Olgaard, K. et al., "Can hyperparathyroid bone disease be arrested or reversed?," Clin J Am Soc Nephrol. (2006) 1(3):367-73. Epub Mar. 29, 2006.
Onyia, J.E. et al., "Molecular profile of catabolic versus anabolic treatment regimens of parathyroid hormone (PTH) in rat bone: an analysis by DNA microarray," J Cell Biochem. (2005) 95(2):403-18.
Owens, R.J. et al., "Mapping the collagen-binding site of human fibronectin by expression in *Escherichia coli*," The EMBO Journal (1986) 5(11)2825-2830.
Paillard, M. et al., "Determinants of parathormone secretion in primary hyperparathyroidism," Horm Res. (1989) 32(1-3):89-92.
Parfitt, A.M., "The actions of parathyroid hormone on bone: relation to bone remodeling and turnover, calcium homeostasis, and metabolic bone disease. Part IV of IV parts: The state of the bones in uremic hyperaparathyroidism—the mechanisms of skeletal resistance to PTH in renal failure and pseudohypoparathyroidism and the role of PTH in osteoporosis, osteopetrosis, and osteofluorosis," Metabolism. (1976) 25(10):1157-88.
Parfitt, A.M. et al., "Hypercalcemia due to constitutive activity of the parathyroid hormone (PTH)/PTH-related peptide receptor: comparison with primary hyperparathyroidism," J Clin Endocrinol Metab. (1996) 81(10):3584-8.
Peters, E.M.J. et al., "A new strategy for modulating chewtherapy-induced alopecia, using PTH/PTHrP receptor agonist and antagonist," J Invest Dermatol (2001) 117(2):173-178.
Pettway, et al., "Anabolic actions of PTH (1-34): Use of a novel tissue engineering model to investigate temporal effects on bone," Bone (2005) 36(6):959-970.

(56) References Cited

OTHER PUBLICATIONS

Phelps, E. et al., "Parathyroid hormone induces receptor activity modifying protein-3 (RAMP3) expression primarily via. 3', 5'-cyclic adenosine monophosphate signaling in osteoblasts," Calcif Tissue Int. (2005) 77(2):96-103 Epub Aug. 11, 2005.
Philominathan et al., "Unidirectional binding of Clostridial Colleagenase to Triple Helical Substrates," Journal of Biological Chemistry (2009) 284(16):10868-10876.
Pirih, F.Q. et al., "Parathyroid hormone induces the NR4A family of nuclear orphan receptors in vivo," Biochem Biophys Res Commun. (2005) 332(2): 494-503.
Podbesek, R. et al., "Effects of two treatment regimes with synthetic human parathyroid hormone fragment on bone formation and the tissue balance of trabecular bone in greyhounds," Endocrinology (1983) 112(3):1000-6.
Poole, K.E. et al., "Parathyroid hormone—a bone anabolic and catabolic agent," Curr Opin Pharmacol. (2005) 5(6):612-7. Epub Sep. 21, 2005.
Watson, P.H. et al., "Enhanced osteoblast development after continuous infusion of hPTH(1-84) in the rat," Bone (1999) 24(2):89-94.
Weir, E.C. et al., "Synthetic parathyroid hormone-like protein (1-74) is anabolic for bone in vivo," Caleif Tissue Int. (1992) 51(1):30-4.
Whitfield, J.F., "Taming Psoriatic Keratinocytes-PTHs' uses go up another notch," J. Cell, Biochem, (2004) 93:251-256.
Wilson, J.J. et al., "A bacterial collagen-binding domain with novel calcium-binding motif controls domain orientation," EMBO Journal (2003) 22(8)1743-1752.
Xu, M. et al., "Basal bone phenotype and increased anabolic responses to intermittent parathyroid hormone in healthy male COX-2 knockout mice," Bone (2010) 47(2):341-52. Epub May 13, 2010.
Yang, C. et al., "Effects of continuous and pulsatile PTH treatments on rat bone marrow stromal cells," Biochem Biophys Res Commun. (2009) 380(4):791-6, Epub Feb. 3, 2009.
Yoshihara, K. et al., "Cloning and nucleotide sequence analysis or the ColH gene from Clostridium histolyticum encoding a collagenase and a gelatinase," J Bacteriol (1994) 176:6489-6496.
Younes, N.A. et al., "Laboratory screening for hyperparathyroidism," Clin Chim Acta. (2005) 353(1-2):1-12.
Zang, X.Y. et al., "Effects of parathyroid hormone and estradiol on proliferation and function of human osteoblasts from fetal long bone: An in vitro study," Chin Med J (Engl). (1994) 107(8):600-3.
Zaruba, M.M. et al., "Parathyroid hormone treatment after myocardial infarction promotes cardiac repair by enhanced neovascularization and cell survival," Cardiovasc Res (2008) 77(4):722-731.
Zhou, H. et al., "Anabolic action of parathyroid hormone on cortical and cancellous bone differs between axial and appendicular skeletal sites in mice," Bone (2003) 32(5):513-520.
International Search Report and Written Opinion of the International Searching Authority for Application No. PCT/US08/004589 dated Oct. 28, 2008 (17 pages).
Extended European Search Report for Application No. 08742686.2 dated Aug. 4, 2010 (8 pages).
United States Patent Office Action for U.S. Appl. No. 12/594,547 dated Aug. 6, 2012 (12 pages).
International Search Report and Written Opinion of the International Searching Authority for Application No. PCT/US12/69831 dated Mar. 14, 2013 (12 pages).
International Search Report and Written Opinion of the International Searching Authority for Application No. PCT/US2013/25541 dated Jun. 17, 2013 (16 pages).
Fukayama, S. et al., "New insights into interactions between the human PTH/PTHrP receptor and agonist/antagonist binding," Am. J. Physiol. Endocrinol. Metab. (1998) 274:297-303.
Gao, V. et al., "T cells potentiate PTH-induced cortical bone loss through CD40L signaling," Cell Metab. (2008) 8(2):132-45.
Gardella, T.J. et al., "Converting Parathyroid Hormone-related Peptide (PTHrP) into a Potent PTH-2 Receptor Agonist," J. of Biological Chemistry, (1996) 271(33):19888-19893.

Gensure, R.C. et al., "Parathyroid hormone and parathyroid hormone-related peptide, and their receptors," Biochem Biophys Res Commun. (2005) 328(1):666-78.
Gensure, R.C. et al., "Parathyroid hormone without parathyroid glands," Endocrinology (2005) 146(2):544-546.
Gevers, E.F.et al., "Bone marrow adipocytes: a neglected target tissue for growth hormone," Endocrinology (2002) 143(10):4065-73.
Goltzman, D., "Studies on the mechanisms of the skeletal anabolic action of endogenous and exogenous parathyroid hormone," Arch Biochem Biophys. (2008) 473(2):218-24. Epub Mar. 10, 2008.
Gopalakrishnan, R. et al., "Role of matrix Gla protein in parathyroid hormone inhibition of osteoblast mineralization," Cells Tissues Organs (2005) 181(3-4):166-75.
Gosavi, A. et al., "An unusual presentation of parathyroid adenoma—a case report," Indian J Pathol Microbiol. (2005) 48(2):208-10.
Gu, W.X. et al., "Mutual up-regulation of thyroid hormone and parathyroid hormone receptors in rat osteoblastic osteosarcoma 17/2.8 cells," Endocrinology (2001) 142(1):157-64.
Hall., A.K. et al., "The effects of parathyroid hormone on osteoblast-like cells from embryonic chick calvaria," Acta Endocrinol (Copenh). (1985) 108(2):217-23.
Han, B. et al., "Collagen-targeted BMP3 fusion proteins arrayed on collagen matrices or porous ceramics impregnated with Type I collagen enhance osteogenesis in a rat cranial defect model," J Orthopaedic Research (2002) 20:747-755.
Headley, C.M., "Hungry bone syndrome following parathyroidectomy," Anna J., (1998) 25(3):283-9; quiz 290-1.
Heath, H., 3rd, "Clinical spectrum of primary hyperparathyroidism: evolution with changes in medical practice and technology," J Bone Miner Res. (1991) 6(Suppl 2):S63-70; discussion S83-4.
Hoare, S.R. et al., "Specificity and stability of a new PTH1 receptor antagonist, mouse TIP(7-39)," Peptides (2002) 23(5):989-998.
Hock, J.M. et al., "Human parathyroid hormone-(1-34) increases bone mass in ovariectomized and orchidectomized rats," Endocrinology (1988) 122(6):2899-2904.
Hock, J.M. et al., "Effects of continuous and intermittent administration and inhibition of resorption on the anabolic response of bone to parathyroid hormone," J Bone Miner Res. (1992) 7(1):65-72.
Holick, M.F. et al., "Topical PTH (1-34) is a novel, safe and effective treatment Air psoriasis: a randomized self-controlled trial and an open trial," British J. Dermatology 149:370-376.
Homme, M. et al., "Differential regulation of RGS-2 by constant and oscillating PTH concentrations," Calcif Tissue Int. (2009) 84(4):305-12. Epub Feb. 20, 2009.
Horwitz, M.J. et al., "Parathyroid hormone-related protein for the treatment of postmenopausal osteoporosis: defining the maximal tolerable dose," J Clin Endocrinol Metab, (2010) 95(3):1279-87.
Horwitz, M.J. et al., "Continuous PTH and PTHrP infusion causes suppression of bone formation and discordant effects on 1,25(OH)2 vitamin D," J Bone Miner Res. (2005) 20(10):1792-803. Epub Jun. 6, 2005.
Hruska, K. A. et al., "Regulation of skeletal remodeling by parathyroid hormone," Contrib Nephrol. (1991) 91:38-42.
IIda-Klein, A. et al., "Short-term continuous infusion of human parathyroid hormone 1-34 fragment is catabolic with decreased trabecular connectivity density accompanied by hypercalcemia in C57BL/J6 mice," J Endocrinol. (2005) 186(3):549-57.
Ishii, H. et al., "Daily intermittent decreases in serum levels of parathyroid hormone have an anabolic-like action on the bones of uremic rats with low-turnover bone and osteomalacia," Bone (2000) 26(2):175-82.
Ishikawa, T. et al., "Delivery of a growth factor fusion protein having collagen-binding activity to wound tissues," Artif. Organs (2003) 27(2):147-154.
Ishikawa, T. et al., "Production of a biologically active epidermal growth factor fusion protein with high collagen affinity," J. Biochem. (2001) 129(4)627-633.
Ishizuya, T. et al., "Parathyroid hormone exerts disparate effects on osteoblast differentiation depending on exposure time in rat osteoblastic cells," J Clin latest. (1997) 99(12)2961-70.

(56) References Cited

OTHER PUBLICATIONS

Ito, M., "Parathyroid hormone and bone quality," Clin Calcium. (2005) 15(12)31-7.
Ito, M., "Parathyroid and bone: Effect of parathyroid hormone on bone quality," Clin Calcium. (2007) 17(12):1858-64.
Jeon, E. et al., "Engineering and application of collagen-binding fibroblast growth factor 2 for sustained release," (2013) J. of Biomed. Materials Research: Part A.
Jilka, R.L., "Molecular and cellular mechanisms of the anabolic effect of intermittent PTH," Bone (2007) 40(6):1434-1446, Epub Apr. 6, 2007.
Jilka, R.L. et al., "Continuous elevation of PTH increases the number of osteoblasts via both osteoclast-dependent and -independent mechanisms," J Bone Miner Res. (2010) 25(11):2427-37.
Kaji, H., "Parathyroid and bone: Effects of parathyroid hormone on bone resorption and formation: differences between intermittent and continuous treatment," Clin Calcium., (2007) 17(12):1836-42.
Katikaneni et al., "Treatment for chemotherapy-induced atopecia in mice using parathyroid hormone agonists and antagonists linked to coolagen binding domain," Int. J. Cancer (2012) 131(5):E813-821.
Kaye, M. et al. "Elective total parathyroidectomy without autotransplant in end-stage renal disease," Kidney Int. (1989) 35(6):1390-9.
Khan, A. et al., "Primary hyperparathyroidism: pathophysiology and impact on bone," Cmaj. (2000) 163(2):184-7
Kido, S. et al., "Mechanism of PTH actions on bone," Clin. Calcium. (2003) 13(1):14-8.
Kistler, H., "Primaty hyperparathyroidism: An analysis of 152 patients with special references to acute life threatening complications (acute hyperparathyroidism)," Schweiz Med Wochenschr, (1976) 106(Suppl 3):1-61.
Kitazawa, R. et al., "Effects of continuous infusion of parathyroid hormone and parathyroid hormone-related peptide on rat bone in vivo: comparative study by histomorphometry," Bone Miner. (1991) 12(3):157-66.
Klempa, I., "Treatment of secondary and tertiary hyperparathyroidism—surgical viewpoints," Chirurg. (1999) 70(10):1089-101.
Koh, A.J. et al., "3',5'-Cyclic adenosine monophosphate activation in osteoblastic cells: effects on parathyroid hormone-1 receptors and osteoblastic differentiation in vitro," Endocrinology (1999) 140(7):3154-62.
Komarova, S.V., "Mathematical model of paracrine interactions between osteoclasts and osteoblasts predicts anabolic action of parathyroid hormone on bone," Endocrinology, (2005) 146(8);3589-95, Epub Apr. 28, 2005.
Kousteni, S. et al., "The cell biology of parathyroid hormone in osteoblasts," Curr Osteoporos. Rep. (2008) 6(2):72-6.
Kroll, M.H., "Parathyroid hormone temporal effects on bone formation and resorption," Bull Math Biol. (2000)62(1):163-88.
Lemaire, V. et al., "Modeling the interactions between osteoblast and osteoclast activities in bone remodeling," J Theor Biol. (2004) 229(3):293-309.
Li, X. et al., "Determination of dual effects of parathyroid hormone on skeletal gene expression in vivo by microarray and network analysis," J Biol. Chem. (2007) 282(45):33086-97. Epub Aug. 9, 2007.
Li, X. et al., "In vivo parathyroid hormone treatments and RNA isolation and analysis," Methods Mol Biol. (2008) 455:79-87.
Liu, J. et al., "Intermittent PTH administration: a novel therapy method for periodontitis-associated alveolar bone loss," Med Hypotheses. (2009) 72(3):294-6. Epub Nov. 30, 2008.
Abdelhadi, M. et al., "Bone Mineral recovery after parathyroidectomy in patients with primary and renal hyperparathyroidism," J Clin Endocrinol Metals. (1998) 83(11):3845-51.
Abe, V. et al., "Enhancement of graft bone healing by intermittent administration of human parathyroid hormone (1-34) in a rat spinal arthrodesis model," Bone (2007) 41(5):775-785.
Abshirini, H.et al., "Pathologic fractures: a neglected clinical feature of parathyroid adenoma," Case 357029, Epub Nov. 29, 2010.

Akimoto, M. et al., "Effects of CB-VEGF-A injection in rat flap models for improved survival," (2013) Plast. Reconstr, Surg. 131(4):717-725.
Aleksyniene, R. et al., "Parathyroid hormone-possible future drug for orthopedic surgery," Medicina (Kaunas) (2004) 40(9):842-9.
Andrade, M.C., et al., "Bone mineral density and bone histomorphometry in children on long-term dialysis," Pediatr Nephrol. (2007) 22(10):1767-72, Epub Aug. 7, 2007.
Barros, S.P., et al., "Parathyroid to hormone protects against periodontitis-associated bone loss," J Dent Res. (2003) 82(10):791-5.
Bauer, R., et al., "Structural of ColH and ColG collagen-binding domains from Clostridium histolyticum," (2013) *Journal of Bacteriology*, 195(2), 318-327.
Bedi, B., et al., "Inhibition of antigen presentation and T cell costimulation blocks PTH-induced bone loss." Ann N Y Acad Sci. (2010) 1192:215-21.
Belinsky, G.S. et al., "Direct measurement of hormone-induced acidification in intact bone," J Bone Miner Res., (2000) 15(3):550-6.
Bellido, T., et al., "Chronic elevation of parathyroid hormone in mice reduces expression of selerostin by osteocytes: a novel mechanism for hormonal control of osteoblastogenesis," Endocrinology (2005) 146(11):4577-83. Epub Aug. 4, 2005.
Bergenstock, M.K. et al., "Parathyroid hormone stimulation of noncanomical Wnt signaling in bone," Ann N Y Acad Sci. (2007) 1116:354-9.
Bergwitz, C. et al., "Rapid desentization of parathyroid hormone dependent adenylate cyclase in perifused human osteosarcoma cells (SaOS-2)," Biochem Biophys Acta. (1994) 1222(3):447-56.
Bianchi, E.N. et al., "Beta-arrestin2 regulates parathyroid hormone effects on a p38 MAPK and NFkappaB gene expression network in osteobtasts" Bone (2009) 45(4):716-25. Epub Jun. 25, 2009.
Bilezikian, J.P. et al., "Asymptomatic primary hyperparathyroidism: new issues new question—bridging the past with the future," J Bone Miner Res. (2002) 17(Suppl 2):N57-67.
Bilezikian, J.P. et al., "Characterization and evaluation of asymptomatic primary hyperparathyrodism," J Bone Miner Res. (1991) 6(Suppl 2):S85-9; discussion S121-4.
Blachowicz, A. et al., "Serum 1-84 and 7-84 parathyroid hormone concentrations and bone in patients with primary Hyperparathyroidism," Langenbecks Arch Surg. (2008) 393(5):709-13, Epub Jul. 11, 2008.
Buargub, M.A. et al., "Prevalence and pattern of renal osteodystrophy in chronic hemodialysis patients: a cross sectional study of 103 patients," Saudi J Kidney Dis Transpl. (2006) 17(3):401-7.
Calvi, L.M. et al., "Activated parathyroid hormone/parathyroid hormone-related protein receptor in osteoblastic cells differentially affects cortical and trabecular bone," J. Clin. Invest. (2001)107:277-286.
Calvi, L.M. et al., "Osteoblastic cells regulate the haematopoietic stem cell niche," Nature (2003) 425:841-846.
Canalis, E., "Effect of hormones and growth factors on alkaline phosphatase activity and collagen synthesis in cultured rat calvariae," Metabolism (1983) 32(1):14-20.
Canalis, E. et al., "Insulin-like growth factor I mediates selective anabolic effects of parathyroid hormone in bone cultures," J Clin Invest. (1989) 83(1):60-5.
Carter, P.H. et al., "Selective and Nonselective Inverse Agonists for Constitutively Active Type-1 Parathyroid Hormone Receptors: Evidence for Altered Receptor Conformations," Endocrinology (2001) 142(4):1534-1545.
Chan, H.W. et al., "Prospective study on dialysis after total parathyroidectomy without autoimplant," Nephrology (2009) 15(4):441-7.
Chen, B. et al., "Homogeneous osteogenesis and bone regeneration by demineralized bone matrix loading with corlagen-targeting bone morphogenetic protein-2," Biomaterials (2007) 28:1027-1035.
Chen, Q. et al., "Effects of an excess and a deficiency of endogenous parathyroid hormone on volumetric bone mineral density and bone

(56) References Cited

OTHER PUBLICATIONS geometry determined by peripheral quantitative computed tomography in female subjects," J Clin Endocrinol Metab. (2003) 88(10):4655-8.
Cherian, P.P. et al., "Role of gap junction, hemichannels, and connexia 43 in mineralizing in response to intermittent and continuous application of parathyroid hormone," Cell Commun Adhes. (2008) 15(1):43-54.
Chevalley, T. et al., "Bone and hormones, Effects of parathyroid hormone on the bone," Presse Med. (1999) 28(10):547-53.
Cohen, A. et al., "Osteoporosis in adult survivors of adolescent cardiac transplantation may be related to hyperparathyroidism, mild renal insufficiency, and increased bone turnover," J Heart Lung Transplant. (2005) 24(6):696-702.
Compston. J.E., "Skeletal actions of intermittent parathyroid hormone: effects on bone remodelling and structure," Bone (2007) 40(6):1447-1452.
Cormier, C., "Parathyroid hormone in osteoporosis," Presse Med. (2006) 35(3 Pt 2):495-501.
Corsi, A. et al., "Osteomalacic and hyperparathyroid changes in fibrous dysplasia of bone: core biopsy studies and clinical correlations," J Bone Miner Res. (2003) 18(7):1235-46.
Cosman, F., "Parathyroid hormone treatment for osteoporosis," Current Opinion in Endocrinology, Diabetes & Obesity (2008) 15:495-501.
Cundy, T. et al., "Hyperparathyroid bone disease in chronic rental failure," Ulster Med J. (1985) 54(Suppl):S34-43.
Datta, N.S. et al., "Distinct roles for mitogen-activated protein kinase phosphatase-1 (MKP-1) and ERK-MAPK in PTH1R signaling during osteoblast proliferation and differentiation," Cell (2010) 22(3):457-66, Epub.
Deal, C., "The use of intermittent human parathyroid hormone as a treatment for osteoporosis," Curr Rheumatol Rep. (2004) 6(1): 49-58.
Demiralp, B. et al., "Anabolic actions of parathyroid hormone during bone growth are dependent on c-fos," Endocrinology (2002) 143(10):4038-47.
Dobnig, H. et al., "The effects of programmed administration of human parathyroid hormone fragment (1-34) on bone histomorphometry and serum chemistry in rats," Endocrinology (1997) 138(11):4607-12.
Drake, M.T. et al., "Parathyroid hormone increases the expression of receptors for epidermal growth factor in UMR 106-01 cells," Endocrinology (1994) 134(4):1733-7.
Endo, K. et al., "1,25-dihydroxyvitamin D3 as well as its analogue OCT lower blood calcium through inhibition of bone resorption in hypercalcemic rats with continuous parathyroid hormone-related peptide infusion," J Bone Miner Res, (2000) 15(1):175-81.
Etoh, M. et al., "Repetition of continuous PTH Treatments followed by periodic withdrawals exerts anabolic effects on rat bone," J Bone Miner Metab. (2010) 28(6):641-649.
Fitzpatrick, L.A, et al., "Acute primary hyperparathyroidism," Am J. Med. (1987) 82(2):275-82.
Fleming, A. et al., "High-throughput in vivo screening for bone anabolic compounds with zebrafish," J Biomol Screen. (2005) 10(8):823-31. Epub Oct. 18, 2005.
Fouda, M.A., "Primary hyperparathyroidism: King Khalid University Hospital Experience," Ann. Saudi Med. (1999) 19(2):110-5.
Fox, J. et al., "Effects of daily treatment with parathyroid hormone 1-84 for 16 months on density, architecture and biomechanical properties of cortical bone in adult ovariectomized rhesus monkeys," Bone (2007) 41(3):321-330.
Fraher, Li et al., "Comparison of the biochemical responses to human parathyroid hormone-(1-31)NH2 and hPTH-(1-34) in healthy humans," J Clin Endocrinol Metab. (1999) 84(8):2739-43.
Frolik, C.A. et al., "Anabolic and catabolic bone effects of human parathyroid hormone (1-34) are predicted by duration of hormone exposure," Bone (2003) 33(3):372-379.
Fujita, T., "Parathyroid hormone in The treatment of osteoporosis," BioDrugs (2001) 15(11):721-728.

Potter, L.K. et al., "Response to continuous and pulsatile PTH dosing: a mathematical model for parathyroid hormone receptor kinetics," Bone (2005) 37(2):159-169.
Potts, J.T., "Parathyroid hormone: past and present," J Endocronology (2005) 187:311-325.
Qin, L. et al., "Parathyroid hormone: a double-edged sword for bone metabolism," Trends Endocrinol Metab. (2004) 15(2):60-5.
Rattanakul, C. et al., "Modeling of bone formation and resorption mediated by parathyroid hormone: response to estrogen/PTH therapy" Biosystems (2003) 70(1):55-72.
Richardson, M.L. et al., "Bone mineral changes in primary hyperparathyroidism," Skeletal Radiol, (1986) 15(2):85-95.
Rickard, D.J. et al., "Intermittent treatment with parathyroid hormone (PTH) as well as a non-peptide small molecule agonist of the PTH1 receptor inhibits adipocyte differentiation in human bone marrow stromal cells," Bone (2006) 39(6):1361-1372. Epub Aug. 10, 2006.
Rixon, R.H. et al., "Parathyroid hormone fragments may stimulate bone growth in ovariectomized rats by activating adenyly cyclase," J Bone Miner Res. (1994) 9(8):1179-89.
Robinson, J.A. et al., "Identification of a PTH regulated gene selectively induced in vivo during PTH-mediated bone formation," J Cell Biochem. (2006) 98(5):1203-20.
Rosen, C.J., "The cellular and clinical parameters of anabolic therapy for osteoporosis," Crit Rev Eukaryot Gene Expr. (2003) 13(1):25-38.
Rubin, M.R. et al., "The potential of parathyroid hormone as it therapy for osteoporosis," Int J Fertil Womens Med. (2002) 47(3):103-15.
Rubin, M. et al., "The anabolic effects of parathyroid hormone therapy," Osteoporosis International (2002) 13(4):267-277.
Rubin, M.R. et al. "The anabolic effects of parathyroid hormone therapy," Clin Geriatr Med. (2003) 19(2):415-32.
Schaefer, F., "Pulsatile parathyroid hormone secretion in health and disease," Novartis Found Symp. (2000) 227:225-39; discussion 239-43.
Schluter, K.-D. et al., "A N-terminal PTHrP peptide fragment void of a PTP/PTHrP-receptor binding domain activates cardiac ETA receptors," British Journal of Pharmacology(2001) 132:427-432.
Schmitt, C.P. et al., "Intermittent administration of parathyroid hormone (1-37) improves growth and bone mineral density in uremic rats," Kidney Int. (2000) 57(4):1484-92.
Schmitt, C.P. et al., "Structural organization and biological relevance of oscillatory parathyroid hormone secretion," Pediatr Nephrol. (2005) 20(3):346-51. Epub Feb. 8, 2005.
Schneider, A. et al., "Skeletal homeostasis in tissue-engineered bone," J Orthop Res. (2003). 21(5):859-64.
Seeman, E. et al., "Reconstructing the skeleton with intermittent parathyroid hormone," Trends Endocrinol Metab. (2001) 12(7):281-3.
Shen, V. et al., "Skeletal effects of parathyroid hormone infusion in ovariectomized rats with or without estrogen repletion," J Bone Miner Res. (2000) 15(4):740-6.
Shinoda, Y. et al., "Mechanisms underlying catabolic and anabolic functions of parathyroid hormone on bone by combination of culture systems of mouse cells," J. of Cellular Biology (2010) 109(4):755-63.
Silver, J. et al., "Harnessing the parathyroids to create stronger bones," Curr Opin Nephrol Hypertens, (2004) 13(4):471-6.
Silverberg, S.J. et al., "Skeletal disease in primary hyperparathyroidism." J Bone Miner Res., (1989) 4(3):283-91.
Skripitz, R. et al., "Parathyroid hormone—a drug for orthopedic surgery?," Acta Orthop Scand. (2004) 75(6):654-62.
Skripitz, R. et al., "Stimulation of implant fixation by parathyroid hormone (1-34)-A histomorphometric comparison of PMMA cement and stainless steel," J Orthrop Res. (2005) 23(6):1266-70. Epub Jun. 16, 2005.
Smajilovic, S. et al., "Effect of intermittent versus continuous parathyroid hormone in the cardiovascular system of rats," Open Cardiovasc. Med. J. (2010) 4:110-6.
Spurney, R.F. et al., "Anabolic effects of a G protein-coupled receptor kinase inhibitor expressed in osteoblasts," J Clin Invest. (2002) 109(10):1361-71.

(56) References Cited

OTHER PUBLICATIONS

Stewart, A.F., "PTHrP(1-36) as a skeletal anabolic agent for the treatment of osteoporosis," Bone (1996) 19(4):303-306.

Stracke, S. et al., "Long-term outcome after total parathyroidectomy for the management of secondary hyperparathyroidism," Nephron Clin Pract. (2009) 111(2):c102-9. Epub Jan. 13, 2009.

Strewler, C.J., "Local and systemic control of the osteoblast," J. of Clin. Invest. (2001) 107:271-272.

Suttamanatwong, S. et al., "Regulation of matrix Gla protein by parathyroid hormone in MC3T3-E1 osteoblast-like cells involves protein kinase A and extracellular signal-regulated kinase pathways," J Cell Biochem. (2007) 102(2):496-505.

Suttamanatwong S. et al., "Sp proteins and Runx2 mediate regulation of matrix gla protein (MGP) expression by parathyroid hormone," J Cell Biochem. (2009) 107(2):284-92.

Suzuki, A. et al., "PTH/cAMP/PKA signaling facilitates canonical Wnt signaling via inactivation of glycogen synthase kinase-3beta in osteoblastic Saos-2 cells," J Cell Biochem. (2008) 104(1):304-17.

Swarthout, J.T. et al., "Parathyroid hormone-dependent signaling pathways regulating genes in bone cells," Gene (2002) 282(1-2):1-17.

Swarthout, J.T. et al., "Stimulation of extracellular signal-regulated kinases and proliferation in rat osteoblastic cells by parathyroid hormone is protein kinase C-dependent," J Biol Chem. (2001) 276(10):7586-92. Epub Dec. 6, 2000.

Takada, H. et al., "Response of parathyroid hormone to anaerobic exercise in adolescent female athletes," Acta Paediatr Jpn. (1998) 40(1):73-7.

Takasu, H. et al., "Dual signaling and ligand selectivity of the human PTH/PTHrP receptor," J Bone Miner Res. (1999) 14(1):11-20.

Talmage, R. V. et al., "Calcium homeostasis: reassessment of the actions of . . . parathyroid hormone," Gen Comp Endocrinol. (2008) 156(1):1-8. Epub Nov. 12, 2007.

Tam, C.S. et al., "Parathyroid hormone stimulates the bone apposition rate independently of its resorptive action: differential effects of intermittent and continuous administration," Endocrinology (1982) 110(2):506-12.

Tawfeek, H. et al., "Disruption of PTH receptor 1 in T cells protects against PTH-induced bone loss," PLoS (2010) 5(8):e12290.

Tokumoto, M. et al., "Parathyroid cell growth in patients with advanced secondary hyperparathyroidism: vitamin D receptor, calcium sensing receptor, and cell cycle regulating factors," Tiler Apher Dial. (2005) 9(Suppl 1):S27-34.

Tollin, S.R. et al., "Serial changes in bone mineral density and bone turnover after correction of secondary hyperparathyroidism in a patient with pseudohypoparathyroidism type lb," J Bone Miner Res. (2000) 15(7):I412-6.

Toyoshima, T. et al., "Collagen-binding domain of a Clostridium histolyticum collagenase exhibits a broad substrate spectrum both in vitro and in vivo," Connective Tissue Research (2001) 42(4):281-290.

Uzawa, T. et al., "Comparison of the effects of intermittent and continuous administration of human parathyroid hormone (1-34) on rat bone," Bone (1995) 16(4):477-84.

Vanstone, M.B. et al., "Rapid correction of bone mass after parathyroidectomy in an adolescent with primary hyperparathyroidism," J. Clin Endocrinol. Metab. (2011) 96(2): E347-50. Epub Nov. 24, 2010.

Wan, Q. et al., "Intra-articular injection parathyroid hormone in the temporomandibular joint as a novel therapy for mandibular asymmetry," Med Hypotheses (2009) 74(4):685-7.

Wang, C.A. et al., "Natural history of parathyroid carcinoma. Diagnosis, treatment, and results," Am J Surg. (1985) 149(4):522-7.

Wang, Y. et al., "A theoretical model for simulating effect of parathyroid hormone on bone metabolism at cellular level," Mol Cell Biomech. (2009) 6(2):101-12.

Wang, Y. et al., "Gentler differences in the response of CD-1 mouse bone to parathyroid hormone: potential role of IGF-1," J Endocrinol. (2006) 189(2):279-87.

* cited by examiner

Fig. 1

```
              3₁₀   A                B              C              D
              ━━━   →                →              →              →
        900         910              920            930            940          950
Co10_s3b      LKEKE NDSSDK VLPNFMTYQ S.LG-DDSEDYTSFE/KEEGEVNIE.DKKDE
Csporogenes_C IHEKE NDSFES KIVLN-APIL SING-EDLEDITSFE KETKD.NIKLTNLNN
Cbotulinum_A3C IYEKE NDSFET KIMLN-TTVL NING-KDVRDISED IKEAKDIDKINNLNN
Bcereus_AH603 LITESE NNRPEE RIGLN-TTIK SLIG-GDHTDVTTTN ASAKNINISVLNEYG
Banthracis    LITESE NNRPEE RIGLN-TTIK SLIG-GDHTDVTTTN ASAKNIDISVLNEYG
BB14905_B     KTEIE NNRPEE MLPFN-TPLS SIME-DDHTDVENTT SPKEIDISVLNENQ
Lsphaericus_B KAEIE NNRPEE ILPFN-TPIK RIMD-DDHTDVENTT SPKEIDISVLNENR
Ccereus_G9842 VTEKE NNEPRQ KVNFH-TPVK TLHN-SDRVDVFTTQ DSPENINISLAEQN
Bmycoides     SVEKE NNSFQT KLQLN-QLIR SIGN-GDTSDYEINT ETARMIQINTKENN
BweihenstephH AVEKE NNSFDA PLSLN-ALLR NISD-QDVCRVFDKD PKDIQITTNEQN
Bbrevis_A     ERKQE NNSFSE PLKSN-VELS QTSK-QDDKIIFALKV LGNGTVKINVTSEHD
Bbrevis_B     PTEVE NNSFDD TLQLG-KEIS QTDR-TDDKDTMIQV EEGVIQVTVSSEKD
Cperfringens_B IKEVE NNDFDK MKVDSN-SKIV TISN-DDLKDISID KNPSDINIVENLDN
Csporogenes_B ISEKE NDSFDK RVGKN-QTVL TLDT-KINNDTYYFD LAARTIDIVENTDN
Cbotulinum_A3B ISEKE NNSFDK RVCKN-QSVI TIDT-NDPDTYYFDA LTAGNIEVTGNTDN
Csporogenes_A VSEKE NNDFTT PVYYK-DLVN SVSS-SDNKDTYYTT KPSDITTTEKTNN
Cbotulinum_A3A VSEKE NNDYVN PVTSK-DLVN SVSS-SDDDIFYNVKF EVKEDAQLNISLKTEG
Csordellii_B  GVEQE NNSFEK PFSIN-QLVK EIDNMKDTSDYKFE KEDAQLNISLKTEG
Co10_s3a      TKEME NDIKE GPIVEGVTVK DING-SUDALTFYFD KEDGDVTIELPYSGS
Cperfringens_A INESE NNDFEK QIAKSNMLVK TLSE-EDYSDKYIDD AKKGNVKITMNLNB
Csordellii_A  SQSVG EDTFET GPIKINTNVS DISD-TDNMKDTYFNL DNPSNINTIEMLDN
                    ━━━
              3₁₀
        870         880            890           900            910          920
Co10_s3b      GTEKE NNSKET GPIVPGIPVS TIEN-TSDQIYFYFDVITPGEVKDINKLGY
```

> Injection

Agonist    Vehicle    Antagonist

Vehicle                           PTH-CBD

Day:  0      1      4         0      1      4

SEQUENCE LISTING

```
<160> NUMBER OF SEQ ID NOS: 47

<210> SEQ ID NO 1
<211> LENGTH: 158
<212> TYPE: PRT
<213> ORGANISM: Artificial Sequence
<220> FEATURE:
<223> OTHER INFORMATION: Synthetic fusion protein containing parathyroid
      hormone segment and collagen-binding domain

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Gly Ile Asn Ser Pro Val Tyr Pro Ile Gly Thr Glu Lys Glu Pro
            35                  40                  45

Asn Asn Ser Lys Glu Thr Ala Ser Gly Pro Ile Val Pro Gly Ile Pro
        50                  55                  60

Val Ser Gly Thr Ile Glu Asn Thr Ser Asp Gln Asp Tyr Phe Tyr Phe
65                  70                  75                  80

Asp Val Ile Thr Pro Gly Glu Val Lys Ile Asp Ile Asn Lys Leu Gly
                85                  90                  95

Tyr Gly Gly Ala Thr Trp Val Val Tyr Asp Glu Asn Asn Asn Ala Val
            100                 105                 110

Ser Tyr Ala Thr Asp Asp Gly Gln Asn Leu Ser Gly Lys Phe Lys Ala
        115                 120                 125

Asp Lys Pro Gly Arg Tyr Tyr Ile His Leu Tyr Met Phe Asn Gly Ser
    130                 135                 140

Tyr Met Pro Tyr Arg Ile Asn Ile Glu Gly Ser Val Gly Arg
145                 150                 155

<210> SEQ ID NO 2
<211> LENGTH: 251
<212> TYPE: PRT
<213> ORGANISM: Artificial Sequence
<220> FEATURE:
<223> OTHER INFORMATION: Synthetic fusion protein containing parathyroid
      hormone fragment and collagen-binding domain and polycystic kidney
      disease domain of ColH.

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Gly Ile Pro Glu Ile Lys Asp Leu Ser Glu Asn Lys Leu Pro Val
            35                  40                  45

Ile Tyr Met His Val Pro Lys Ser Gly Ala Leu Asn Gln Lys Val Val
        50                  55                  60

Phe Tyr Gly Lys Gly Thr Tyr Asp Pro Asp Gly Ser Ile Ala Gly Tyr
65                  70                  75                  80

Gln Trp Asp Phe Gly Asp Gly Ser Asp Phe Ser Ser Glu Gln Asn Pro
                85                  90                  95

Ser His Val Tyr Thr Lys Lys Gly Glu Tyr Thr Val Thr Leu Arg Val
```

```
              100                 105                 110
Met Asp Ser Ser Gly Gln Met Ser Glu Lys Thr Met Lys Ile Lys Ile
                115                 120                 125

Thr Asp Pro Val Tyr Pro Ile Gly Thr Glu Lys Glu Pro Asn Asn Ser
            130                 135                 140

Lys Glu Thr Ala Ser Gly Pro Ile Val Pro Gly Ile Pro Val Ser Gly
145                 150                 155                 160

Thr Ile Glu Asn Thr Ser Asp Gln Asp Tyr Phe Tyr Phe Asp Val Ile
                165                 170                 175

Thr Pro Gly Glu Val Lys Ile Asp Ile Asn Lys Leu Gly Tyr Gly Gly
            180                 185                 190

Ala Thr Trp Val Val Tyr Asp Glu Asn Asn Asn Ala Val Ser Tyr Ala
                195                 200                 205

Thr Asp Asp Gly Gln Asn Leu Ser Gly Lys Phe Lys Ala Asp Lys Pro
            210                 215                 220

Gly Arg Tyr Tyr Ile His Leu Tyr Met Phe Asn Gly Ser Tyr Met Pro
225                 230                 235                 240

Tyr Arg Ile Asn Ile Glu Gly Ser Val Gly Arg
                245                 250

<210> SEQ ID NO 3
<211> LENGTH: 5464
<212> TYPE: DNA
<213> ORGANISM: Artificial Sequence
<220> FEATURE:
<223> OTHER INFORMATION: Synthetic expression vector

<400> SEQUENCE: 3
agcttatcga ctgcacggtg caccaatgct tctggcgtca ggcagccatc ggaagctgtg      60
gtatggctgt gcaggtcgta aatcactgca taattcgtgt cgctcaaggc gcactcccgt     120
tctggataat gttttttgcg ccgacatcat aacggttctg gcaaatattc tgaaatgagc     180
tgttgacaat taatcatcgg ctcgtataat gtgtggaatt gtgagcggat aacaatttca     240
cacaggaaac agtattcatg tcccctatac taggttattg gaaaattaag ggccttgtgc     300
aacccactcg acttcttttg gaatatcttg aagaaaaata tgaagagcat ttgtatgagc     360
gcgatgaagg tgataaatgg cgaaacaaaa agtttgaatt gggtttggag tttcccaatc     420
ttccttatta tattgatggt gatgttaaat taacacagtc tatggccatc atacgttata     480
tagctgacaa gcacaacatg ttgggtggtt gtccaaaaga gcgtgcagag atttcaatgc     540
ttgaaggagc ggttttggat attagatacg gtgtttcgag aattgcatat agtaaagact     600
tgaaactctc aaagttgat tttcttagca agctacctga aatgctgaaa atgttcgaag     660
atcgtttatg tcataaaaca tatttaaatg gtgatcatgt aacccatcct gacttcatgt     720
tgtatgacgc tcttgatgtt gttttataca tggacccaat gtgcctggat gcgttcccaa     780
aattagtttg ttttaaaaaa cgtattgaag ctatcccaca aattgataag tacttgaaat     840
ccagcaagta tatagcatgg cctttgcagg gctggcaagc cacgtttggt ggtggcgacc     900
atcctccaaa atcggatctg atcgaaggtc gttctgtgag tgaaatacag cttatgcata     960
acctgggaaa acatctgaac tcgatggaga gagtagaatg gctgcgtaag aagctgcagg    1020
atgtgcacaa tggaattaat tccccggtat atccaatagg cactgaaaaa gaaccaaata    1080
acagtaaaga aactgcaagt ggtccaatag taccaggtat acctgttagt ggaaccatag    1140
aaaatacaag tgatcaagat tatttctatt ttgatgttat aacaccagga gaagtaaaaa    1200
```

```
tagatataaa taaattaggg tacggaggag ctacttgggt agtatatgat gaaaataata      1260
atgcagtatc ttatgccact gatgatgggc aaaatttaag tggaaagttt aaggcagata      1320
aaccaggtag atattacatc catctttaca tgtttaatgg tagttatatg ccatatagaa      1380
ttaatataga aggttcagta ggaagataat attttattag ttgaggtaac tccactcgaa      1440
ttggtcgact cgagcggccg catcgtgact gactgacgat ctgcctcgcg cgtttcggtg      1500
atgacggtga aaacctctga cacatgcagc tcccggagac ggtcacagct tgtctgtaag      1560
cggatgccgg gagcagacaa gcccgtcagg gcgcgtcagc gggtgttggc gggtgtcggg      1620
gcgcagccat gacccagtca cgtagcgata gcggagtgta taattcttga agacgaaagg      1680
gcctcgtgat acgcctattt ttataggtta atgtcatgat aataatggtt tcttagacgt      1740
caggtggcac ttttcgggga atgtgcgcg gaaccctat ttgtttattt ttctaaatac        1800
attcaaatat gtatccgctc atgagacaat aaccctgata aatgcttcaa taatattgaa      1860
aaaggaagag tatgagtatt caacatttcc gtgtcgccct tattccctt tttgcggcat       1920 tttgccttcc tgttttgct cacccagaaa cgctggtgaa agtaaaagat gctgaagatc        1980
agttgggtgc acgagtgggt tacatcgaac tggatctcaa cagcggtaag atccttgaga      2040
gttttcgccc cgaagaacgt tttccaatga tgagcacttt taaagttctg ctatgtggcg      2100
cggtattatc ccgtgttgac gccgggcaag agcaactcgg tcgccgcata cactattctc      2160
agaatgactt ggttgagtac tcaccagtca cagaaaagca tcttacggat ggcatgacag      2220
taagagaatt atgcagtgct gccataacca tgagtgataa cactgcggcc aacttacttc      2280
tgacaacgat cggaggaccg aaggagctaa ccgcttttt gcacaacatg ggggatcatg       2340
taactcgcct tgatcgttgg gaaccggagc tgaatgaagc cataccaaac gacgagcgtg      2400
acaccacgat gcctgcagca atggcaacaa cgttgcgcaa actattaact ggcgaactac      2460
ttactctagc ttcccggcaa caattaatag actggatgga ggcggataaa gttgcaggac      2520
cacttctgcg ctcggccctt ccggctggct ggtttattgc tgataaatct ggagccggtg      2580
agcgtgggtc tcgcggtatc attgcagcac tggggccaga tggtaagccc tcccgtatcg      2640
tagttatcta cacgacgggg agtcaggcaa ctatggatga acgaaataga cagatcgctg      2700
agataggtgc ctcactgatt aagcattggt aactgtcaga ccaagtttac tcatatatac      2760
tttagattga tttaaaactt cattttttaat ttaaaaggat ctaggtgaag atcctttttg     2820
ataatctcat gaccaaaatc ccttaacgtg agttttcgtt ccactgagcg tcagaccccg      2880
tagaaaagat caaaggatct tcttgagatc cttttttttct gcgcgtaatc tgctgcttgc     2940
aaacaaaaaa accaccgcta ccagcggtgg tttgtttgcc ggatcaagag ctaccaactc      3000 ttttttccgaa ggtaactggc ttcagcagag cgcagatacc aaatactgtc cttctagtgt     3060
agccgtagtt aggccaccac ttcaagaact ctgtagcacc gcctacatac ctcgctctgc      3120
taatcctgtt accagtggct gctgccagtg gcgataagtc gtgtcttacc gggttggact      3180
caagacgata gttaccggat aaggcgcagc ggtcgggctg aacggggggt tcgtgcacac      3240
agcccagctt ggagcgaacg acctacaccg aactgagata cctacagcgt gagctatgag      3300
aaagcgccac gcttcccgaa gggagaaagg cggacaggta tccggtaagc ggcagggtcg      3360
gaacaggaga gcgcacgagg gagcttccag ggggaaacgc ctggtatctt tatagtcctg      3420
tcgggtttcg ccacctctga cttgagcgtc gatttttgtg atgctcgtca ggggggcgga      3480
gcctatggaa aaacgccagc aacgcggcct ttttacggtt cctggccttt tgctggcctt      3540
ttgctcacat gttctttcct gcgttatccc ctgattctgt ggataaccgt attaccgcct      3600
```

```
ttgagtgagc tgataccgct cgccgcagcc gaacgaccga gcgcagcgag tcagtgagcg      3660
aggaagcgga agagcgcctg atgcggtatt ttctccttac gcatctgtgc ggtatttcac      3720
accgcataaa ttccgacacc atcgaatggt gcaaaacctt cgcggtatg  gcatgatagc      3780 gcccggaaga gagtcaattc agggtggtga atgtgaaacc agtaacgtta tacgatgtcg      3840
cagagtatgc cggtgtctct tatcagaccg tttcccgcgt ggtgaaccag gccagccacg      3900
tttctgcgaa aacgcgggaa aaagtggaag cggcgatggc ggagctgaat tacattccca      3960
accgcgtggc acaacaactg gcgggcaaac agtcgttgct gattggcgtt gccacctcca      4020
gtctggccct gcacgcgccg tcgcaaattg tcgcggcgat taaatctcgc gccgatcaac      4080
tgggtgccag cgtggtggtg tcgatggtag aacgaagcgg cgtcgaagcc tgtaaagcgg      4140
cggtgcacaa tcttctcgcg caacgcgtca gtgggctgat cattaactat ccgctggatg      4200
accaggatgc cattgctgtg gaagctgcct gcactaatgt tccggcgtta tttcttgatg      4260
tctctgacca gacacccatc aacagtatta ttttctccca tgaagacggt acgcgactgg      4320
gcgtggagca tctggtcgca ttgggtcacc agcaaatcgc gctgttagcg ggcccattaa      4380
gttctgtctc ggcgcgtctg cgtctggctg gctggcataa atatctcact cgcaatcaaa      4440
ttcagccgat agcggaacgg gaaggcgact ggagtgccat gtccggtttt caacaaacca      4500
tgcaaatgct gaatgagggc atcgttccca ctgcgatgct ggttgccaac gatcagatgg      4560
cgctgggcgc aatgcgcgcc attaccgagt ccgggctgcg cgttggtgcg gatatctcgg      4620
tagtgggata cgacgatacc gaagacagct catgttatat cccgccgtta accaccatca      4680
aacaggattt tcgcctgctg ggcaaaacca gcgtggaccg cttgctgcaa ctctctcagg      4740
gccaggcggt gaagggcaat cagctgttgc ccgtctcact ggtgaaaaga aaaccaccc       4800 tggcgcccaa tacgcaaacc gcctctcccc gcgcgttggc cgattcatta atgcagctgg      4860
cacgacaggt ttcccgactg gaaagcgggc agtgagcgca acgcaattaa tgtgagttag      4920
ctcactcatt aggcaccca  ggctttacac tttatgcttc cggctcgtat gttgtgtgga      4980
attgtgagcg gataacaatt tcacacagga aacagctatg accatgatta cggattcact      5040
ggccgtcgtt ttacaacgtc gtgactggga aaaccctggc gttacccaac ttaatcgcct      5100
tgcagcacat ccccctttcg ccagctggcg taatagcgaa gaggcccgca ccgatcgccc      5160
ttcccaacag ttgcgcagcc tgaatggcga atggcgcttt gcctggtttc cggcaccaga      5220
agcggtgccg gaaagctggc tggagtgcga tcttcctgag gccgatactg tcgtcgtccc      5280
ctcaaactgg cagatgcacg gttacgatgc gcccatctac accaacgtaa cctatcccat      5340
tacggtcaat ccgccgtttg ttcccacgga gaatccgacg gttgttact  cgctcacatt      5400 taatgttgat gaaagctggc tacaggaagg ccagacgcga attattttg  atggcgttgg      5460 aatt                                                                   5464
```

<210> SEQ ID NO 4
<211> LENGTH: 383
<212> TYPE: PRT
<213> ORGANISM: Artificial Sequence
<220> FEATURE:
<223> OTHER INFORMATION: Synthetic GST-PTH-CBD fusion protein

<400> SEQUENCE: 4

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu

|   |   |   |   |   | 20 |   |   |   |   | 25 |   |   |   |   | 30 |   |
|---|---|---|---|---|---|---|---|---|---|---|---|---|---|---|---|---|

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Ile Glu Gly
    210                 215                 220

Arg Ser Val Ser Glu Ile Gln Leu Met His Asn Leu Gly Lys His Leu
225                 230                 235                 240

Asn Ser Met Glu Arg Val Glu Trp Leu Arg Lys Lys Leu Gln Asp Val
                245                 250                 255

His Asn Gly Ile Asn Ser Pro Val Tyr Pro Ile Gly Thr Glu Lys Glu
            260                 265                 270

Pro Asn Asn Ser Lys Glu Thr Ala Ser Gly Pro Ile Val Pro Gly Ile
            275                 280                 285

Pro Val Ser Gly Thr Ile Glu Asn Thr Ser Asp Gln Asp Tyr Phe Tyr
    290                 295                 300

Phe Asp Val Ile Thr Pro Gly Glu Val Lys Ile Asp Ile Asn Lys Leu
305                 310                 315                 320

Gly Tyr Gly Gly Ala Thr Trp Val Val Tyr Asp Glu Asn Asn Asn Ala
                325                 330                 335

Val Ser Tyr Ala Thr Asp Asp Gly Gln Asn Leu Ser Gly Lys Phe Lys
            340                 345                 350

Ala Asp Lys Pro Gly Arg Tyr Tyr Ile His Leu Tyr Met Phe Asn Gly
            355                 360                 365

Ser Tyr Met Pro Tyr Arg Ile Asn Ile Glu Gly Ser Val Gly Arg
    370                 375                 380

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide: Factor Xa recognition
      sequence

<400> SEQUENCE: 5

Ile Glu Gly Arg
1

<210> SEQ ID NO 6
<211> LENGTH: 1021
<212> TYPE: PRT
<213> ORGANISM: Clostridium histolyticum

<400> SEQUENCE: 6

Met Lys Arg Lys Cys Leu Ser Lys Arg Leu Met Leu Ala Ile Thr Met
1               5                   10                  15

Ala Thr Ile Phe Thr Val Asn Ser Thr Leu Pro Ile Tyr Ala Ala Val
            20                  25                  30

Asp Lys Asn Asn Ala Thr Ala Ala Val Gln Asn Glu Ser Lys Arg Tyr
        35                  40                  45

Thr Val Ser Tyr Leu Lys Thr Leu Asn Tyr Tyr Asp Leu Val Asp Leu
    50                  55                  60

Leu Val Lys Thr Glu Ile Glu Asn Leu Pro Asp Leu Phe Gln Tyr Ser
65                  70                  75                  80

Ser Asp Ala Lys Glu Phe Tyr Gly Asn Lys Thr Arg Met Ser Phe Ile
                85                  90                  95

Met Asp Glu Ile Gly Arg Arg Ala Pro Gln Tyr Thr Glu Ile Asp His
            100                 105                 110

Lys Gly Ile Pro Thr Leu Val Glu Val Val Arg Ala Gly Phe Tyr Leu
        115                 120                 125

Gly Phe His Asn Lys Glu Leu Asn Glu Ile Asn Lys Arg Ser Phe Lys
    130                 135                 140

Glu Arg Val Ile Pro Ser Ile Leu Ala Ile Gln Lys Asn Pro Asn Phe
145                 150                 155                 160

Lys Leu Gly Thr Glu Val Gln Asp Lys Ile Val Ser Ala Thr Gly Leu
                165                 170                 175

Leu Ala Gly Asn Glu Thr Ala Pro Pro Glu Val Val Asn Asn Phe Thr
            180                 185                 190

Pro Ile Leu Gln Asp Cys Ile Lys Asn Ile Asp Arg Tyr Ala Leu Asp
        195                 200                 205

Asp Leu Lys Ser Lys Ala Leu Phe Asn Val Leu Ala Ala Pro Thr Tyr
    210                 215                 220

Asp Ile Thr Glu Tyr Leu Arg Ala Thr Lys Glu Lys Pro Glu Asn Thr
225                 230                 235                 240

Pro Trp Tyr Gly Lys Ile Asp Gly Phe Ile Asn Glu Leu Lys Lys Leu
                245                 250                 255

Ala Leu Tyr Gly Lys Ile Asn Asp Asn Asn Ser Trp Ile Ile Asp Asn
            260                 265                 270

Gly Ile Tyr His Ile Ala Pro Leu Gly Lys Leu His Ser Asn Asn Lys
        275                 280                 285

Ile Gly Ile Glu Thr Leu Thr Glu Val Met Lys Val Tyr Pro Tyr Leu
    290                 295                 300

Ser Met Gln His Leu Gln Ser Ala Asp Gln Ile Lys Arg His Tyr Asp
305                 310                 315                 320

Ser Lys Asp Ala Glu Gly Asn Lys Ile Pro Leu Asp Lys Phe Lys Lys
                325                 330                 335

Glu Gly Lys Glu Lys Tyr Cys Pro Lys Thr Tyr Thr Phe Asp Asp Gly
            340                 345                 350

Lys Val Ile Ile Lys Ala Gly Ala Arg Val Glu Glu Lys Val Lys
        355                 360                 365

```
Arg Leu Tyr Trp Ala Ser Lys Glu Val Asn Ser Gln Phe Phe Arg Val
    370                 375                 380

Tyr Gly Ile Asp Lys Pro Leu Glu Glu Gly Asn Pro Asp Asp Ile Leu
385                 390                 395                 400

Thr Met Val Ile Tyr Asn Ser Pro Glu Glu Tyr Lys Leu Asn Ser Val
                405                 410                 415

Leu Tyr Gly Tyr Asp Thr Asn Asn Gly Gly Met Tyr Ile Glu Pro Glu
            420                 425                 430

Gly Thr Phe Phe Thr Tyr Glu Arg Glu Ala Gln Glu Ser Thr Tyr Thr
        435                 440                 445

Leu Glu Glu Leu Phe Arg His Glu Tyr Thr His Tyr Leu Gln Gly Arg
    450                 455                 460

Tyr Ala Val Pro Gly Gln Trp Gly Arg Thr Lys Leu Tyr Asp Asn Asp
465                 470                 475                 480

Arg Leu Thr Trp Tyr Glu Gly Gly Ala Glu Leu Phe Ala Gly Ser
                485                 490                 495

Thr Arg Thr Ser Gly Ile Leu Pro Arg Lys Ser Ile Val Ser Asn Ile
            500                 505                 510

His Asn Thr Thr Arg Asn Asn Arg Tyr Lys Leu Ser Asp Thr Val His
        515                 520                 525

Ser Lys Tyr Gly Ala Ser Phe Glu Phe Tyr Asn Tyr Ala Cys Met Phe
    530                 535                 540

Met Asp Tyr Met Tyr Asn Lys Asp Met Gly Ile Leu Asn Lys Leu Asn
545                 550                 555                 560

Asp Leu Ala Lys Asn Asn Asp Val Asp Gly Tyr Asp Asn Tyr Ile Arg
                565                 570                 575

Asp Leu Ser Ser Asn Tyr Ala Leu Asn Asp Lys Tyr Gln Asp His Met
            580                 585                 590

Gln Glu Arg Ile Asp Asn Tyr Glu Asn Leu Thr Val Pro Phe Val Ala
        595                 600                 605

Asp Asp Tyr Leu Val Arg His Ala Tyr Lys Asn Pro Asn Glu Ile Tyr
    610                 615                 620

Ser Glu Ile Ser Glu Val Ala Lys Leu Lys Asp Ala Lys Ser Glu Val
625                 630                 635                 640

Lys Lys Ser Gln Tyr Phe Ser Thr Phe Thr Leu Arg Gly Ser Tyr Thr
                645                 650                 655

Gly Gly Ala Ser Lys Gly Lys Leu Glu Asp Gln Lys Ala Met Asn Lys
            660                 665                 670

Phe Ile Asp Asp Ser Leu Lys Lys Leu Asp Thr Tyr Ser Trp Ser Gly
        675                 680                 685

Tyr Lys Thr Leu Thr Ala Tyr Phe Thr Asn Tyr Lys Val Asp Ser Ser
    690                 695                 700

Asn Arg Val Thr Tyr Asp Val Val Phe His Gly Tyr Leu Pro Asn Glu
705                 710                 715                 720

Gly Asp Ser Lys Asn Ser Leu Pro Tyr Gly Lys Ile Asn Gly Thr Tyr
                725                 730                 735

Lys Gly Thr Glu Lys Glu Lys Ile Lys Phe Ser Ser Glu Gly Ser Phe
            740                 745                 750

Asp Pro Asp Gly Lys Ile Val Ser Tyr Glu Trp Asp Phe Gly Asp Gly
        755                 760                 765

Asn Lys Ser Asn Glu Glu Asn Pro Glu His Ser Tyr Asp Lys Val Gly
    770                 775                 780
```

```
Thr Tyr Thr Val Lys Leu Lys Val Thr Asp Asp Lys Gly Glu Ser Ser
785                 790                 795                 800

Val Ser Thr Thr Thr Ala Glu Ile Lys Asp Leu Ser Glu Asn Lys Leu
            805                 810                 815

Pro Val Ile Tyr Met His Val Pro Lys Ser Gly Ala Leu Asn Gln Lys
        820                 825                 830

Val Val Phe Tyr Gly Lys Gly Thr Tyr Asp Pro Asp Gly Ser Ile Ala
    835                 840                 845

Gly Tyr Gln Trp Asp Phe Asp Gly Ser Asp Phe Ser Ser Glu Gln
850                 855                 860

Asn Pro Ser His Val Tyr Thr Lys Gly Glu Tyr Thr Val Thr Leu
865                 870                 875                 880

Arg Val Met Asp Ser Ser Gly Gln Met Ser Glu Lys Thr Met Lys Ile
            885                 890                 895

Lys Ile Thr Asp Pro Val Tyr Pro Ile Gly Thr Glu Lys Glu Pro Asn
            900                 905                 910

Asn Ser Lys Glu Thr Ala Ser Gly Pro Ile Val Pro Gly Ile Pro Val
            915                 920                 925

Ser Gly Thr Ile Glu Asn Thr Ser Asp Gln Asp Tyr Phe Tyr Phe Asp
930                 935                 940

Val Ile Thr Pro Gly Glu Val Lys Ile Asp Ile Asn Lys Leu Gly Tyr
945                 950                 955                 960

Gly Gly Ala Thr Trp Val Val Tyr Asp Glu Asn Asn Asn Ala Val Ser
                965                 970                 975

Tyr Ala Thr Asp Asp Gly Gln Asn Leu Ser Gly Lys Phe Lys Ala Asp
            980                 985                 990

Lys Pro Gly Arg Tyr Tyr Ile His Leu Tyr Met Phe Asn Gly Ser Tyr
        995                 1000                1005

Met Pro Tyr Arg Ile Asn Ile Glu Gly Ser Val Gly Arg
    1010                1015                1020

<210> SEQ ID NO 7
<211> LENGTH: 84
<212> TYPE: PRT
<213> ORGANISM: Homo sapiens

<400> SEQUENCE: 7

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 8
<211> LENGTH: 141
<212> TYPE: PRT
<213> ORGANISM: Homo sapiens

<400> SEQUENCE: 8

Ala Val Ser Glu His Gln Leu Leu His Asp Lys Gly Lys Ser Ile Gln
```

```
                1               5                  10                 15
        Asp Leu Arg Arg Arg Phe Phe Leu His His Leu Ile Ala Glu Ile His
                   20                  25                  30

Thr Ala Glu Ile Arg Ala Thr Ser Glu Val Ser Pro Asn Ser Lys Pro
                   35                  40                  45

Ser Pro Asn Thr Lys Asn His Pro Val Arg Phe Gly Ser Asp Asp Glu
            50                  55                  60

Gly Arg Tyr Leu Thr Gln Glu Thr Asn Lys Val Glu Thr Tyr Lys Glu
        65                  70                  75                  80

Gln Pro Leu Lys Thr Pro Gly Lys Lys Lys Gly Lys Pro Gly Lys
                        85                  90                  95

Arg Lys Glu Gln Glu Lys Lys Arg Arg Thr Arg Ser Ala Trp Leu
                       100                 105                 110

Asp Ser Gly Val Thr Gly Ser Gly Leu Glu Gly Asp His Leu Ser Asp
                       115                 120                 125

Thr Ser Thr Thr Ser Leu Glu Leu Asp Ser Arg Arg His
                       130                 135                 140
```

<210> SEQ ID NO 9
<211> LENGTH: 160
<212> TYPE: PRT
<213> ORGANISM: Artificial Sequence
<220> FEATURE:
<223> OTHER INFORMATION: Synthetic Gly-Ser-PTH(1-33)-CBD fusion protein

<400> SEQUENCE: 9

```
        Gly Ser Ser Val Ser Glu Ile Gln Leu Met His Asn Leu Gly Lys His
        1               5                  10                  15

Leu Asn Ser Met Glu Arg Val Glu Trp Leu Arg Lys Lys Leu Gln Asp
                    20                  25                  30

Val His Asn Gly Ile Asn Ser Pro Val Tyr Pro Ile Gly Thr Glu Lys
                    35                  40                  45

Glu Pro Asn Asn Ser Lys Glu Thr Ala Ser Gly Pro Ile Val Pro Gly
            50                  55                  60

Ile Pro Val Ser Gly Thr Ile Glu Asn Thr Ser Asp Gln Asp Tyr Phe
        65                  70                  75                  80

Tyr Phe Asp Val Ile Thr Pro Gly Glu Val Lys Ile Asp Ile Asn Lys
                    85                  90                  95

Leu Gly Tyr Gly Gly Ala Thr Trp Val Val Tyr Asp Glu Asn Asn Asn
                    100                 105                 110

Ala Val Ser Tyr Ala Thr Asp Asp Gly Gln Asn Leu Ser Gly Lys Phe
                    115                 120                 125

Lys Ala Asp Lys Pro Gly Arg Tyr Tyr Ile His Leu Tyr Met Phe Asn
                    130                 135                 140

Gly Ser Tyr Met Pro Tyr Arg Ile Asn Ile Glu Gly Ser Val Gly Arg
        145                 150                 155                 160
```

<210> SEQ ID NO 10
<211> LENGTH: 152
<212> TYPE: PRT
<213> ORGANISM: Artificial Sequence
<220> FEATURE:
<223> OTHER INFORMATION: Synthetic PTH(7-33)-CBD fusion protein

<400> SEQUENCE: 10

```
        Leu Met His Asn Leu Gly Lys His Leu Asn Ser Met Glu Arg Val Glu
        1               5                  10                  15
```

```
Trp Leu Arg Lys Lys Leu Gln Asp Val His Asn Gly Ile Asn Ser Pro
            20                  25                  30

Val Tyr Pro Ile Gly Thr Glu Lys Glu Pro Asn Asn Ser Lys Glu Thr
        35                  40                  45

Ala Ser Gly Pro Ile Val Pro Gly Ile Pro Val Ser Gly Thr Ile Glu
 50                  55                  60

Asn Thr Ser Asp Gln Asp Tyr Phe Tyr Phe Asp Val Ile Thr Pro Gly
 65                  70                  75                  80

Glu Val Lys Ile Asp Ile Asn Lys Leu Gly Tyr Gly Gly Ala Thr Trp
                85                  90                  95

Val Val Tyr Asp Glu Asn Asn Asn Ala Val Ser Tyr Ala Thr Asp Asp
            100                 105                 110

Gly Gln Asn Leu Ser Gly Lys Phe Lys Ala Asp Lys Pro Gly Arg Tyr
        115                 120                 125

Tyr Ile His Leu Tyr Met Phe Asn Gly Ser Tyr Met Pro Tyr Arg Ile
    130                 135                 140

Asn Ile Glu Gly Ser Val Gly Arg
145                 150

<210> SEQ ID NO 11
<211> LENGTH: 35
<212> TYPE: PRT
<213> ORGANISM: Artificial Sequence
<220> FEATURE:
<223> OTHER INFORMATION: Synthetic PTH(1-33) with Gly-Ser amino terminal
      extension

<400> SEQUENCE: 11

Gly Ser Ser Val Ser Glu Ile Gln Leu Met His Asn Leu Gly Lys His
 1               5                  10                  15

Leu Asn Ser Met Glu Arg Val Glu Trp Leu Arg Lys Lys Leu Gln Asp
            20                  25                  30

Val His Asn
        35

<210> SEQ ID NO 12
<211> LENGTH: 6
<212> TYPE: PRT
<213> ORGANISM: Artificial Sequence
<220> FEATURE:
<223> OTHER INFORMATION: Synthetic thrombin cleavage sequence

<400> SEQUENCE: 12

Leu Val Pro Arg Gly Ser
 1               5

<210> SEQ ID NO 13
<211> LENGTH: 111
<212> TYPE: PRT
<213> ORGANISM: Clostridium histolyticum

<400> SEQUENCE: 13

Leu Lys Glu Lys Glu Asn Asn Asp Ser Ser Asp Lys Ala Thr Val Ile
 1               5                  10                  15

Pro Asn Phe Asn Thr Thr Met Gln Gly Ser Leu Leu Gly Asp Asp Ser
            20                  25                  30

Arg Asp Tyr Tyr Ser Phe Glu Val Lys Glu Glu Gly Glu Val Asn Ile
        35                  40                  45

Glu Leu Asp Lys Lys Asp Glu Phe Gly Val Thr Trp Thr Leu His Pro
 50                  55                  60
```

Glu Ser Asn Ile Asn Asp Arg Ile Thr Tyr Gly Gln Val Asp Gly Asn
65                  70                  75                  80

Lys Val Ser Asn Lys Val Lys Leu Arg Pro Gly Lys Tyr Tyr Leu Leu
            85                  90                  95

Val Tyr Lys Tyr Ser Gly Ser Gly Asn Tyr Glu Leu Arg Val Asn
        100                 105                 110

<210> SEQ ID NO 14
<211> LENGTH: 111
<212> TYPE: PRT
<213> ORGANISM: C. sporogenes

<400> SEQUENCE: 14

Ile His Glu Lys Glu Asn Asn Asp Ser Phe Glu Ser Ala Asn Lys Ile
1               5                   10                  15

Val Leu Asn Ala Pro Ile Leu Gly Ser Leu Asn Gly Glu Asp Leu Arg
            20                  25                  30

Asp Ile Tyr Ser Phe Glu Ile Lys Glu Thr Lys Asp Leu Asn Ile Lys
        35                  40                  45

Leu Thr Asn Leu Asn Asn Leu Gly Leu Thr Trp Thr Leu Tyr Lys Glu
    50                  55                  60

Ser Asp Leu Asn Asn Tyr Ile Ala Tyr Gly Ser Lys Leu Gly Ser Thr
65                  70                  75                  80

Ile Val Gly Asn Cys His Val Thr Pro Gly Lys Tyr Tyr Leu Tyr Val
            85                  90                  95

Tyr Lys Tyr Ser Gly Asn Asn Gly Asn Tyr Ser Leu Ile Ile Lys
        100                 105                 110

<210> SEQ ID NO 15
<211> LENGTH: 111
<212> TYPE: PRT
<213> ORGANISM: C. botulinum

<400> SEQUENCE: 15

Ile Tyr Glu Lys Glu Asn Asn Asp Ser Phe Glu Thr Ala Asn Lys Ile
1               5                   10                  15

Met Leu Asn Thr Thr Val Leu Gly Asn Leu Asn Gly Lys Asp Val Arg
            20                  25                  30

Asp Ile Tyr Ser Phe Asp Ile Lys Glu Ala Lys Asp Leu Asp Ile Lys
        35                  40                  45

Leu Asn Asn Leu Asn Asn Leu Gly Leu Ala Trp Asn Leu Tyr Lys Glu
    50                  55                  60

Ser Asp Leu Asn Asn Tyr Ile Ala Tyr Gly Ser Val Ser Gly Asn Thr
65                  70                  75                  80

Ile Lys Gly Lys Cys Asn Val Ala Pro Gly Lys Tyr Tyr Leu Tyr Val
            85                  90                  95

Tyr Lys Tyr Ser Gly Asp Asn Gly Asn Tyr Ser Leu Ala Ile Lys
        100                 105                 110

<210> SEQ ID NO 16
<211> LENGTH: 111
<212> TYPE: PRT
<213> ORGANISM: B. cereus

<400> SEQUENCE: 16

Leu Thr Glu Ser Glu Pro Asn Asn Arg Pro Glu Glu Ala Asn Arg Ile
1               5                   10                  15

Gly Leu Asn Thr Thr Ile Lys Gly Ser Leu Ile Gly Gly Asp His Thr
            20                  25                  30

Asp Val Tyr Thr Phe Asn Val Ala Ser Ala Lys Asn Ile Asn Ile Ser
            35                  40                  45

Val Leu Asn Glu Tyr Gly Ile Gly Met Thr Trp Val Leu His His Glu
        50                  55                  60

Ser Asp Met Gln Asn Tyr Ala Ala Tyr Gly Gln Val Asn Gly Asn His
65                  70                  75                  80

Ile Glu Ala Asn Phe Asn Ala Lys Pro Gly Lys Tyr Tyr Leu Tyr Val
                85                  90                  95

Tyr Lys Tyr Asp Asn Gly Asp Gly Thr Tyr Glu Leu Ser Val Lys
            100                 105                 110

<210> SEQ ID NO 17
<211> LENGTH: 111
<212> TYPE: PRT
<213> ORGANISM: B. anthracis

<400> SEQUENCE: 17

Leu Thr Glu Ser Glu Pro Asn Asn Arg Pro Glu Glu Ala Asn Arg Ile
1               5                   10                  15

Gly Leu Asn Thr Thr Ile Lys Gly Ser Leu Ile Gly Gly Asp His Thr
            20                  25                  30

Asp Val Tyr Thr Phe Asn Val Ala Ser Ala Lys Asn Ile Asp Ile Ser
            35                  40                  45

Val Leu Asn Glu Tyr Gly Ile Gly Met Thr Trp Val Leu His His Glu
        50                  55                  60

Ser Asp Met Gln Asn Tyr Ala Ala Tyr Gly Gln Ala Asn Gly Asn His
65                  70                  75                  80

Ile Glu Ala Asn Phe Asn Ala Lys Pro Gly Lys Tyr Tyr Leu Tyr Val
                85                  90                  95

Tyr Lys Tyr Asp Asn Gly Asp Gly Thr Tyr Glu Leu Ser Val Lys
            100                 105                 110

<210> SEQ ID NO 18
<211> LENGTH: 111
<212> TYPE: PRT
<213> ORGANISM: Bacillus sp.

<400> SEQUENCE: 18

Lys Thr Glu Ile Glu Pro Asn Asn Arg Pro Glu Glu Ala Thr Met Leu
1               5                   10                  15

Pro Phe Asn Thr Pro Leu Ser Gly Ser Leu Met Glu Asp Asp His Thr
            20                  25                  30

Asp Val Tyr Glu Phe Asn Val Thr Ser Pro Lys Glu Ile Asp Ile Ser
            35                  40                  45

Val Leu Asn Glu Asn Gln Ile Gly Met Thr Trp Val Leu Tyr His Glu
        50                  55                  60

Ser Asp Ser Gln Asn Tyr Ala Ser Phe Gly Gln Glu Asp Gly Asn Met
65                  70                  75                  80

Ile Asn Gly Lys Trp Asn Ala Lys Pro Gly Lys Tyr Tyr Leu Tyr Val
                85                  90                  95

Tyr Lys Phe Glu Asn Glu Asn Gly Thr Tyr Thr Val His Val Gln
            100                 105                 110

<210> SEQ ID NO 19
<211> LENGTH: 111

<212> TYPE: PRT
<213> ORGANISM: L. sphaericus

<400> SEQUENCE: 19

```
Lys Ala Glu Ile Glu Pro Asn Asn Arg Pro Glu Glu Ala Thr Ile Leu
1               5                   10                  15

Pro Phe Asn Thr Pro Leu Lys Gly Arg Leu Met Asp Asp Asp His Thr
            20                  25                  30

Asp Val Tyr Glu Phe Asn Val Thr Ser Pro Lys Glu Leu Asp Ile Ser
        35                  40                  45

Val Leu Asn Glu Asn Arg Ile Gly Met Thr Trp Val Leu Tyr His Glu
    50                  55                  60

Ser Asp Ser Gln Asn Tyr Ala Ser Phe Gly Gln Glu Glu Gly Asn Met
65                  70                  75                  80

Ile Asn Gly Lys Leu His Ala Glu Pro Gly Lys Tyr Tyr Leu Tyr Val
                85                  90                  95

Tyr Lys Phe Glu Asn Glu Asn Gly Thr Tyr Thr Val Gln Val Gln
            100                 105                 110
```

<210> SEQ ID NO 20
<211> LENGTH: 111
<212> TYPE: PRT
<213> ORGANISM: C. cerus

<400> SEQUENCE: 20

```
Val Thr Glu Asn Glu Pro Asn Asn Glu Pro Arg Gln Ala Asn Lys Val
1               5                   10                  15

Asn Phe His Thr Pro Val Lys Gly Thr Leu His Asn Ser Asp Arg Val
            20                  25                  30

Asp Val Phe Thr Phe Gln Ile Asp Ser Pro Glu Asn Ile Asn Ile Ser
        35                  40                  45

Leu Leu Asn Glu Gln Asn Ile Gly Met Thr Trp Val Leu His His Glu
    50                  55                  60

Ser Asp Leu Asn Asn Tyr Val Ala Tyr Gly Glu Asn Glu Gly Asn Val
65                  70                  75                  80

Val Lys Gly Thr Tyr Asn Ala Lys Pro Gly Lys Tyr Tyr Leu Tyr Val
                85                  90                  95

Tyr Lys Tyr Glu Asn Lys Asp Gly Ser Tyr Val Leu Asn Ile Lys
            100                 105                 110
```

<210> SEQ ID NO 21
<211> LENGTH: 111
<212> TYPE: PRT
<213> ORGANISM: B. mycoides

<400> SEQUENCE: 21

```
Ser Val Glu Lys Glu Pro Asn Asn Ser Phe Gln Thr Ala Asn Lys Leu
1               5                   10                  15

Gln Leu Asn Gln Leu Leu Arg Ala Ser Leu Gly Asn Gly Asp Thr Ser
            20                  25                  30

Asp Tyr Phe Glu Ile Asn Val Glu Thr Ala Arg Asn Leu Gln Ile Asn
        35                  40                  45

Val Thr Lys Glu Asn Asn Ile Gly Val Asn Trp Val Leu Tyr Ser Ala
    50                  55                  60

Ala Asp Leu Asn Asn Tyr Val Thr Tyr Ala Gln Thr Gln Gly Asn Lys
65                  70                  75                  80

Leu Val Gly Ser Tyr Asn Ala His Pro Gly Lys Tyr Tyr Leu His Val
```

```
                    85                  90                  95

Tyr Gln Tyr Gly Gly Gly Thr Gly Asn Tyr Thr Val Glu Val Lys
            100                 105                 110

<210> SEQ ID NO 22
<211> LENGTH: 112
<212> TYPE: PRT
<213> ORGANISM: B. weihensteph

<400> SEQUENCE: 22

Ala Val Glu Lys Glu Pro Asn Asn Ser Phe Asp Ala Ala Asn Pro Leu
1               5                   10                  15

Ser Leu Asn Ala Leu Leu Arg Gly Asn Leu Ser Asp Gln Asp Gln Val
            20                  25                  30

Asp Arg Phe Val Ile Asp Val Lys Asp Pro Lys Asp Leu Gln Ile Thr
        35                  40                  45

Val Thr Asn Glu Gln Asn Leu Gly Leu Asn Trp Val Leu Tyr Ser Glu
    50                  55                  60

Ser Asp Leu Asn Asn Tyr Val Thr Tyr Ala Thr Lys Arg Asp Gly Asn
65                  70                  75                  80

Lys Leu Leu Gly Asn Tyr Asn Ala Lys Pro Gly Lys Tyr Tyr Leu Ser
                85                  90                  95

Val Tyr Lys Tyr Gly Gly Gly Thr Gly Asn Phe Thr Val Glu Val Lys
            100                 105                 110

<210> SEQ ID NO 23
<211> LENGTH: 111
<212> TYPE: PRT
<213> ORGANISM: B. brevis

<400> SEQUENCE: 23

Glu Lys Glu Gln Glu Pro Asn Asn Ser Phe Ser Glu Ala Asn Pro Leu
1               5                   10                  15

Lys Ser Asn Val Glu Leu Ser Gly Gln Thr Ser Lys Gln Asp Asp Lys
            20                  25                  30

Asp Ile Phe Ala Leu Lys Val Leu Gly Asn Gly Thr Val Lys Ile Asn
        35                  40                  45

Val Thr Ser Glu His Asp Thr Gly Leu Asn Trp Val Val His His Glu
    50                  55                  60

Asp Asp Leu Asn Asn Tyr Leu Ala Tyr Pro Lys Thr Ser Gly Lys Thr
65                  70                  75                  80

Leu Ser Gly Glu Phe Glu Ala Thr Pro Gly Tyr Tyr Leu Ser Val
                85                  90                  95

Tyr Asn Phe Asn Gly Glu Thr Ile Pro Tyr Lys Val Thr Ala Glu
            100                 105                 110

<210> SEQ ID NO 24
<211> LENGTH: 111
<212> TYPE: PRT
<213> ORGANISM: B. brevis

<400> SEQUENCE: 24

Pro Thr Glu Val Glu Pro Asn Asn Ser Phe Asp Ala Asn Thr Leu
1               5                   10                  15

Gln Leu Gly Lys Glu Ile Ser Gly Gln Thr Asp Arg Thr Asp Asp Lys
            20                  25                  30

Asp Thr Tyr Met Ile Gln Val Glu Glu Gly Val Ile Gln Val Thr
        35                  40                  45
```

Val Ser Ser Glu Lys Asp Glu Gly Leu Asn Trp Val Val Phe His Glu
    50                  55                  60

Asp Asp Leu Lys Thr Tyr Phe Ala Tyr Pro Lys Thr Thr Gly Lys Lys
 65                  70                  75                  80

Leu Thr Gly Glu Phe Glu Ala Lys Pro Gly Lys Tyr Tyr Leu Leu Val
                85                  90                  95

Tyr Asn Thr Asn Asn Thr Lys Ile Pro Tyr Lys Ala Ile Val Asn
                100                 105                 110

<210> SEQ ID NO 25
<211> LENGTH: 112
<212> TYPE: PRT
<213> ORGANISM: C. perfringens

<400> SEQUENCE: 25

Ile Lys Glu Val Glu Asn Asn Asp Phe Asp Lys Ala Met Lys Val
 1               5                  10                  15

Asp Ser Asn Ser Lys Ile Val Gly Thr Leu Ser Asn Asp Leu Lys
                20                  25                  30

Asp Ile Tyr Ser Ile Asp Ile Lys Asn Pro Ser Asp Leu Asn Ile Val
                35                  40                  45

Val Glu Asn Leu Asp Asn Ile Lys Met Asn Trp Leu Leu Tyr Ser Ala
    50                  55                  60

Asp Asp Leu Ser Asn Tyr Val Asp Tyr Ala Asn Ala Asp Gly Asn Lys
 65                  70                  75                  80

Leu Ser Asn Thr Cys Lys Leu Asn Pro Gly Lys Tyr Tyr Leu Cys Val
                85                  90                  95

Tyr Gln Phe Glu Asn Ser Gly Thr Gly Asn Tyr Thr Val Asn Leu Gln
                100                 105                 110

<210> SEQ ID NO 26
<211> LENGTH: 115
<212> TYPE: PRT
<213> ORGANISM: C. sporogenes

<400> SEQUENCE: 26

Ile Ser Glu Lys Glu Asp Asn Asp Ser Phe Asp Lys Ala Asn Arg Val
 1               5                  10                  15

Gly Lys Asn Gln Thr Val Leu Ala Thr Leu Asp Thr Lys Asp Asn Arg
                20                  25                  30

Asp Thr Tyr Tyr Phe Asp Ala Leu Ala Ala Arg Thr Ile Asp Ile Val
                35                  40                  45

Met Glu Asn Thr Asp Asn Asn Ser Thr Ile Phe Asn Trp Leu Ala Tyr
    50                  55                  60

Ser Ser Asp Asn Thr Asn Asn Tyr Ile Gly Tyr Pro Thr Lys Lys Glu
 65                  70                  75                  80

Gly Asn Lys Leu Met Gly Ser Phe Lys Val Pro Lys Pro Gly Arg Tyr
                85                  90                  95

Tyr Ile Leu Ala Tyr Lys Asn Ser Ser Asn Lys Ile Asn Tyr Lys Leu
                100                 105                 110

Thr Ile Asn
        115

<210> SEQ ID NO 27
<211> LENGTH: 115
<212> TYPE: PRT
<213> ORGANISM: C. botulinum

```
<400> SEQUENCE: 27

Ile Ser Glu Lys Glu Asp Asn Asn Ser Phe Asp Lys Ala Asn Arg Val
1               5                   10                  15

Cys Lys Asn Gln Ser Val Ile Ala Thr Leu Asp Thr Asn Asp Pro Arg
            20                  25                  30

Asp Thr Tyr Tyr Phe Asp Ala Leu Thr Ala Gly Asn Ile Glu Val Thr
        35                  40                  45

Met Gly Asn Thr Asp Asn Ser Ser Asn Glu Phe Asn Trp Leu Ala Tyr
50                  55                  60

Ser Ser Asp Asn Thr Asn Asn Tyr Ile Gly Tyr Ala Thr Lys Arg Glu
65                  70                  75                  80

Gly Asn Lys Ile Thr Gly Asn Phe Lys Val Asp Lys Pro Gly Arg Tyr
                85                  90                  95

Tyr Ile Val Ala Tyr Lys Thr Ser Ser Asn Lys Ile Asn Tyr Lys Leu
            100                 105                 110

Asn Ile Lys
        115

<210> SEQ ID NO 28
<211> LENGTH: 115
<212> TYPE: PRT
<213> ORGANISM: C. sporogenes

<400> SEQUENCE: 28

Val Ser Glu Lys Glu Asp Asn Asn Asp Phe Thr Thr Ala Asn Pro Val
1               5                   10                  15

Tyr Tyr Lys Asp Leu Val Asn Gly Ser Val Ser Ser Asp Asn Lys
            20                  25                  30

Asp Thr Phe Tyr Phe Thr Val Thr Lys Pro Ser Asp Ile Thr Ile Thr
        35                  40                  45

Val Glu Lys Thr Asn Asn Asp Lys Ser Glu Phe Asn Trp Leu Leu Phe
50                  55                  60

Ser Asp Glu Asp Lys Ser Asn Tyr Met Ala Phe Pro Asn Lys Glu Leu
65                  70                  75                  80

Gly Asn Gln Leu Ser Asn Thr Val Lys Ile Asn Lys Pro Gly Lys Tyr
                85                  90                  95

Tyr Leu Val Ile Tyr Lys Thr Leu Gly Glu Lys Val Asp Tyr Lys Phe
            100                 105                 110

Ser Ile Glu
        115

<210> SEQ ID NO 29
<211> LENGTH: 115
<212> TYPE: PRT
<213> ORGANISM: C. botulinum

<400> SEQUENCE: 29

Val Ser Glu Lys Glu Asn Asn Asp Tyr Val Asn Ala Asn Pro Val
1               5                   10                  15

Tyr Ser Lys Asp Leu Val Asn Gly Ser Val Ser Ser Asp Asp Arg
            20                  25                  30

Asp Ile Phe Tyr Phe Asn Val Thr Lys Pro Ser Asp Ile Thr Ile Asn
        35                  40                  45

Val Glu Lys Ile Asn Lys Asp Lys Ser Glu Phe Ser Trp Leu Leu Phe
50                  55                  60
```

```
Ser Glu Glu Asp Lys Ser Asn Tyr Ile Thr Tyr Pro Asn Lys Glu Leu
 65                  70                  75                  80

Glu Asn Leu Phe Tyr Ser Thr Val Lys Ile Asp Lys Pro Gly Lys Tyr
                 85                  90                  95

Tyr Leu Val Ile Tyr Lys Val Ser Gly Glu Lys Ser Asp Tyr Arg Phe
            100                 105                 110

Asn Ile Glu
        115

<210> SEQ ID NO 30
<211> LENGTH: 113
<212> TYPE: PRT
<213> ORGANISM: C. sordellii

<400> SEQUENCE: 30

Gly Val Glu Gln Glu Asp Asn Asn Ser Phe Glu Lys Ala Asn Pro Phe
 1               5                  10                  15

Ser Ile Asn Gln Leu Val Lys Gly Glu Leu Asp Asn Asn Lys Asp Thr
                20                  25                  30

Ser Asp Tyr Phe Lys Phe Glu Val Lys Glu Asp Ala Gln Leu Asn Ile
            35                  40                  45

Ser Leu Glu Lys Thr Glu Gly Asp Gly Val Asn Trp Leu Leu Phe Lys
 50                  55                  60

Asp Ser Asp Leu Glu Asn Tyr Ile Ala Ser Pro Thr Glu Ser Ile Asp
 65                  70                  75                  80

Asn Lys Leu Asn Gly Lys Val Asp Leu Lys Val Gly Thr Tyr Tyr Leu
                 85                  90                  95

Glu Val Tyr Gly Tyr Gly Ser Ser Pro Val Lys Tyr Asn Phe Lys Val
            100                 105                 110

Thr

<210> SEQ ID NO 31
<211> LENGTH: 113
<212> TYPE: PRT
<213> ORGANISM: Clostridium histolyticum

<400> SEQUENCE: 31

Thr Lys Glu Met Glu Pro Asn Asp Asp Ile Lys Glu Ala Asn Gly Pro
 1               5                  10                  15

Ile Val Glu Gly Val Thr Val Lys Gly Asp Leu Asn Gly Ser Asp Asp
                20                  25                  30

Ala Asp Thr Phe Tyr Phe Asp Val Lys Glu Asp Gly Asp Val Thr Ile
            35                  40                  45

Glu Leu Pro Tyr Ser Gly Ser Ser Asn Phe Thr Trp Leu Val Tyr Lys
 50                  55                  60

Glu Gly Asp Asp Gln Asn His Ile Ala Ser Gly Ile Asp Lys Asn Asn
 65                  70                  75                  80

Ser Lys Val Gly Thr Phe Lys Ser Thr Lys Gly Arg His Tyr Val Phe
                 85                  90                  95

Ile Tyr Lys His Asp Ser Ala Ser Asn Ile Ser Tyr Ser Leu Asn Ile
            100                 105                 110

Lys

<210> SEQ ID NO 32
<211> LENGTH: 113
<212> TYPE: PRT
<213> ORGANISM: C. perfringens
```

<400> SEQUENCE: 32

```
Ile Asn Glu Ser Glu Pro Asn Asn Asp Phe Glu Lys Ala Asn Gln Ile
1               5                   10                  15

Ala Lys Ser Asn Met Leu Val Lys Gly Thr Leu Ser Glu Glu Asp Tyr
            20                  25                  30

Ser Asp Lys Tyr Tyr Phe Asp Val Ala Lys Lys Gly Asn Val Lys Ile
        35                  40                  45

Thr Leu Asn Asn Leu Asn Ser Val Gly Ile Thr Trp Thr Leu Tyr Lys
    50                  55                  60

Glu Gly Asp Leu Asn Asn Tyr Val Leu Tyr Ala Thr Gly Asn Glu Gly
65                  70                  75                  80

Thr Val Leu Lys Gly Glu Lys Thr Leu Glu Pro Gly Arg Tyr Tyr Leu
                85                  90                  95

Ser Val Tyr Thr Tyr Asp Asn Gln Ser Gly Ala Tyr Thr Val Asn Val
            100                 105                 110

Lys
```

<210> SEQ ID NO 33
<211> LENGTH: 113
<212> TYPE: PRT
<213> ORGANISM: C. sordellii

<400> SEQUENCE: 33

```
Ser Gln Glu Val Gly Asn Asp Asp Thr Phe Glu Thr Ala Asn Gly Pro
1               5                   10                  15

Ile Lys Ile Asn Thr Asn Tyr Ser Gly Asp Leu Ser Asp Thr Asp Asn
            20                  25                  30

Lys Asp Tyr Tyr Tyr Phe Asn Leu Asp Asn Pro Ser Asn Ile Asn Ile
        35                  40                  45

Thr Leu Glu Asn Leu Asp Asn Lys Gly Ile Ser Trp Gln Leu Phe His
    50                  55                  60

Glu Ser Asp Leu Asn Asn Tyr Val Ala Tyr Pro Thr Thr Ser Gly Ala
65                  70                  75                  80

Ile Leu Asn Gly Asp Tyr Asn Ala Thr Lys Pro Gly Lys Tyr Tyr Ile
                85                  90                  95

Leu Val Tyr Asn His Asp Lys Ser Ile Ala Asn Tyr Asn Leu Lys Val
            100                 105                 110

Asn
```

<210> SEQ ID NO 34
<211> LENGTH: 111
<212> TYPE: PRT
<213> ORGANISM: Clostridium histolyticum

<400> SEQUENCE: 34

```
Gly Thr Glu Lys Glu Pro Asn Asn Ser Lys Glu Thr Ala Ser Gly Pro
1               5                   10                  15

Ile Val Pro Gly Ile Pro Val Ser Gly Thr Ile Glu Asn Thr Ser Asp
            20                  25                  30

Gln Asp Tyr Phe Tyr Phe Asp Val Ile Thr Pro Gly Glu Val Lys Ile
        35                  40                  45

Asp Ile Asn Lys Leu Gly Tyr Gly Gly Ala Thr Trp Val Val Tyr Asp
    50                  55                  60

Glu Asn Asn Asn Ala Val Ser Tyr Ala Thr Asp Asp Gly Gln Asn Leu
65                  70                  75                  80
```

```
Ser Gly Lys Phe Lys Ala Asp Lys Pro Gly Arg Tyr Tyr Ile His Leu
             85                  90                  95

Tyr Met Phe Asn Gly Ser Tyr Met Pro Tyr Arg Ile Asn Ile Glu
            100                 105                 110

<210> SEQ ID NO 35
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(30)
<223> OTHER INFORMATION: Any Xaa is hydroxyproline

<400> SEQUENCE: 35

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(30)
<223> OTHER INFORMATION: Any Xaa is hydroxyproline

<400> SEQUENCE: 36

Pro Xaa Gly Pro Xaa Gly Pro Xaa Gly Pro Xaa Gly Pro Xaa Gly Pro
1               5                   10                  15

Xaa Gly Pro Xaa Ala Pro Xaa Gly Pro Xaa Gly Pro Xaa Gly
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(30)
<223> OTHER INFORMATION: Any Xaa is hydroxyproline

<400> SEQUENCE: 37

Pro Xaa Gly Pro Xaa Gly Pro Xaa Gly Pro Xaa Gly Pro Xaa Gly Pro
1               5                   10                  15

Xaa Ala Pro Xaa Gly Pro Xaa Gly Pro Xaa Gly Pro Xaa Gly
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(30)
<223> OTHER INFORMATION: Any Xaa is hydroxyproline
```

```
<400> SEQUENCE: 38

Pro Xaa Gly Pro Xaa Gly Pro Xaa Gly Pro Xaa Gly Pro Xaa Ala Pro
1               5                   10                  15

Xaa Gly Pro Xaa Gly Pro Xaa Gly Pro Xaa Gly Pro Xaa Gly
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(30)
<223> OTHER INFORMATION: Any Xaa is hydroxyproline

<400> SEQUENCE: 39

Pro Xaa Gly Pro Xaa Gly Pro Xaa Gly Pro Xaa Ala Pro Xaa Gly Pro
1               5                   10                  15

Xaa Gly Pro Xaa Gly Pro Xaa Gly Pro Xaa Gly Pro Xaa Gly
            20                  25                  30

<210> SEQ ID NO 40
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(24)
<223> OTHER INFORMATION: Any Xaa is hydroxyproline

<400> SEQUENCE: 40

Pro Xaa Gly Pro Xaa Gly Pro Xaa Gly Pro Cys Gly Pro Xaa Gly Pro
1               5                   10                  15

Xaa Gly Pro Xaa Gly Pro Xaa Gly
            20

<210> SEQ ID NO 41
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(31)
<223> OTHER INFORMATION: Any Xaa is hydroxyproline

<400> SEQUENCE: 41

Pro Xaa Gly Pro Xaa Gly Pro Xaa Gly Pro Xaa Gly Pro Xaa Ala Pro
1               5                   10                  15

Xaa Gly Pro Xaa Gly Pro Xaa Gly Pro Xaa Gly Pro Xaa Gly Cys
            20                  25                  30

<210> SEQ ID NO 42
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(22)
<223> OTHER INFORMATION: Any Xaa is hydroxyproline
```

```
<400> SEQUENCE: 42

Gly Pro Xaa Gly Pro Xaa Gly Pro Xaa Gly Pro Xaa Gly Pro Xaa Gly
1               5                   10                  15

Pro Xaa Gly Pro Xaa Gly
            20

<210> SEQ ID NO 43
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(31)
<223> OTHER INFORMATION: Any Xaa is hydroxyproline

<400> SEQUENCE: 43

Gly Pro Xaa Gly Pro Xaa Gly Pro Xaa Gly Pro Xaa Gly Pro Xaa Gly
1               5                   10                  15

Pro Xaa Gly Pro Xaa Gly Pro Arg Gly Pro Arg Gly Pro Arg Gly
            20                  25                  30

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(9)
<223> OTHER INFORMATION: Any Xaa is hydroxyproline

<400> SEQUENCE: 44

Pro Xaa Gly Pro Xaa Gly Pro Xaa Gly
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(9)
<223> OTHER INFORMATION: Any Xaa is hydroxyproline

<400> SEQUENCE: 45

Pro Xaa Gly Pro Xaa Gly Pro Xaa Ala
1               5

<210> SEQ ID NO 46
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(26)
<223> OTHER INFORMATION: Any Xaa is hydroxyproline

<400> SEQUENCE: 46

Gly Pro Arg Gly Pro Xaa Gly Pro Xaa Gly Pro Xaa Gly Pro Xaa Gly
1               5                   10                  15
```

```
Pro Xaa Gly Pro Xaa Gly Pro Xaa Gly Cys
            20                  25

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide: GST Tag

<400> SEQUENCE: 47

Gly Ser Pro Gly Ile Pro Gly
1               5
```

DELIVERY OF THERAPEUTIC AGENTS BY A COLLAGEN BINDING PROTEIN

CROSS-REFERENCE TO RELATED APPLICATIONS

This patent application is a national stage filing under 35 U.S.C. of International Application No. PCT/US2013/025541, filed Feb. 11, 2013, which claims the benefit of priority of U.S. Provisional Patent Application No. 61/596,869, filed Feb. 9, 2012, and of International Application No. PCT/US2012/069831, filed Dec. 14, 2012, all of which are incorporated herein by reference in their entireties.

STATEMENT REGARDING FEDERALLY SPONSORED RESEARCH

This invention was made with United States government support awarded by the National Institutes of Health grant number NCRR COBRE 8P30GM103450 and INBRE GM103429. The United States may have certain rights in this invention.

SEQUENCE LISTING

A Sequence Listing accompanies this application and is incorporated herein by reference in its entirety. The Sequence Listing was filed with the application as a text file on Feb. 11, 2013.

INTRODUCTION

Delivery of therapeutic agents to sites within the body of a subject where a particular therapeutic agent is needed in order to be effective is a developing area. Such delivery systems will allow more efficient use of therapeutic agents while reducing toxicity caused by some therapeutic agents. Use of targeted liposomes or polypeptides, such as antibodies, to target therapeutic agents to particular sites within the body has proved successful, but additional delivery agents are needed.

Alopecia (hair loss) is a psychologically and emotionally distressing event with multiple causes. Alopecia occurs most commonly in male-pattern baldness, affecting approximately two thirds of males by age 35; a similar pattern of hair loss can be observed in females with polycystic ovarian syndrome. In both of these disorders, the hair loss is androgen mediated. Alopecia can also occur as an autoimmune disease, termed alopecia areata; a disorder which affects 1.7% of the population. It can occur as a side-effect of medical treatments, particularly in chemotherapy, with 65-85% of chemotherapy patients experiencing some degree of alopecia. Psychological consequences of hair loss have been well studied in the chemotherapy setting. Chemotherapy-induced alopecia (CIA) can result in anxiety, depression, a negative body image, lowered self-esteem and a reduced sense of well-being. In fact, 47-58% of female cancer patients consider hair loss to be the most traumatic aspect of chemotherapy, and 8% would decline treatment for fear of hair loss. In addition to these studies in chemotherapy patients, evidence exists in other forms of alopecia to support therapy to reduce psychological consequences of hair loss. Thus a new treatment to stop hair loss or speed hair regrowth would be beneficial.

While drugs with mild anti-androgenic effects (i.e. spironolactone) had been used with limited success as therapy for alopecia, the first effective medication for alopecia was minoxidil (Rogaine). This antihypertensive has an observed side-effect of causing hair growth, and is now used as topical therapy for many forms of alopecia. However, responses are incomplete, with some subjects showing only slowing of hair loss rather than actual regrowth. Finasteride (Propecia) is a newer agent that blocks conversion of testosterone to dihydrotestosterone, resulting in improvements in androgenic alopecia at the expense of partial systemic androgen blockade. However, response rates with long-term (10 years) therapy are only around 50%. Overall, despite considerable research in this area, there is still no adequate therapy for hair loss.

In addition, unwanted hair growth is a cosmetic issue many people deal with on a regular basis. Unwanted hair growth on the face, legs, arms, chest or back is a growing cosmetic problem. Many people use laser therapy, waxing or other therapies to remove unwanted hair. There are currently no topical pharmaceuticals to limit hair growth.

SUMMARY

Provided herein are methods of delivering therapeutic agents by administering compositions including a bacterial collagen-binding polypeptide segment linked to the therapeutic agent to subjects in need of treatment with the therapeutic agent.

In one aspect, methods of treating hyperparathyroidism by administering a composition comprising a bacterial collagen-binding polypeptide segment linked to a PTH/PTHrP receptor agonist to a subject are provided.

In a further aspect, methods of slowing hair growth or regrowth after removal by administering a composition comprising a bacterial collagen-binding polypeptide segment linked to a PTH/PTHrP receptor antagonist to a subject are provided.

In a still further aspect, methods of increasing hair growth or the speed of hair re-growth after removal or loss by administering a composition comprising a bacterial collagen-binding polypeptide segment linked to a PTH/PTHrP receptor agonist to a subject are provided.

BRIEF DESCRIPTION OF THE DRAWINGS

FIG. 1 is a sequence alignment showing the alignment of several M9B bacterial collagenases from the *Bacillus* and *Clostridium* families. The sequences are also provided in the Sequence Listing, filed herewith as follows: ColG s3b (SEQ ID NO: 13); Csporogenes C (SEQ ID NO: 14): CbotulinumA3C (SEQ ID NO: 15); Bcereus_AH603 (SEQ ID NO: 16); Banthracis (SEQ ID NO: 17); BB14905 B (SEQ ID NO: 18): Lsphaericus B (SEQ ID NO: 19); CcereusG9842 (SEQ ID NO: 20); Bmycoides (SEQ ID NO: 21); Bweihensteph (SEQ ID NO: 22): Bbrevis A (SEQ ID NO: 23); Bbrevis B (SEQ ID NO: 24): CperfringensB (SEQ ID NO: 25); Csporogenes B (SEQ ID NO: 26): CbotulinumA3B (SEQ ID NO: 27); Csporogenes A (SEQ ID NO: 28); CbotulinumA3A (SEQ ID NO: 29): Csordellii B (SEQ ID NO: 30); Col

DETAILED DESCRIPTION

Figure 2:
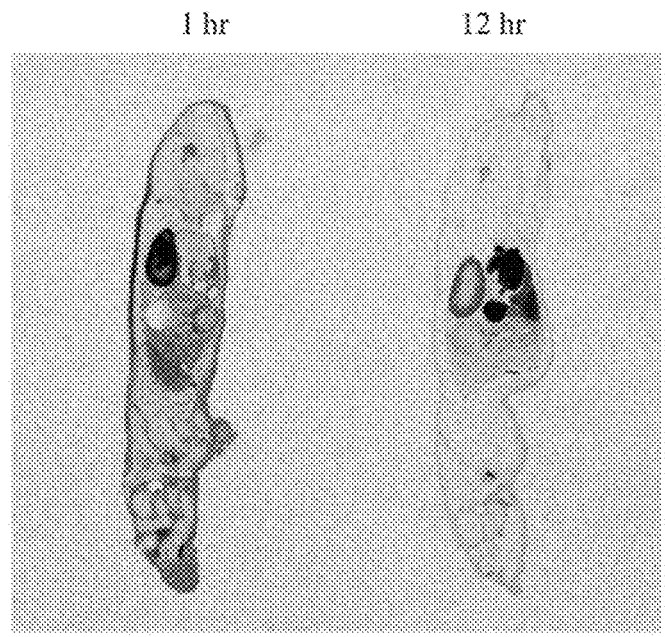
FIG. 2 shows the tissue distribution of $S^{35}$-PTH-CBD 1 hour and 12 hours after subcutaneous injection. Note the skin outline.

The effects of PTH agonists and antagonists on hair growth have been studied for over almost 15 years. PTH has a common receptor with PTH-related peptide (PTHrP), which is normally produced by dermal fibroblasts. PTHrP affects keratinocyte proliferation/differentiation and modulates the hair cycle. Most of the testing on hair growth effects has been performed with PTH antagonists, as indications from initial testing were that these were the most effective agents. Both injected and topical formulations have been tested in animal models of chemotherapy-induced alopecia and in the SKH-1 hairless mouse. Part of the effect of PTH antagonists on hair growth is to transition the hair follicles into a dystrophic catagen stage, which protects them from chemotherapeutic damage. However, clinical trials of topical PTH antagonists for chemotherapy-induced alopecia by MI Pharmaceuticals were discontinued in phase 2 because of limited efficacy. Thus new compositions for treating alopecia are needed.

The problems of delivery and retention of PTH to the skin can be overcome by using collagen-targeted PTH analogs. To accomplish this, we synthesized several fusion proteins of different PTH agonists and antagonists linked to a collagen binding domain derived from the ColH1 collagenase of *Clostridium histolyticum*, in the studies described in the Examples, we found that the agonist compound PTH-CBD promotes transition of hair follicles to the anagen phase and has potent effects on hair growth. The antagonist compound PTH(7-33)-CBD had little effect on hair growth in chemotherapy models and had a deleterious effect on hair regrowth after depilation. Compounds such as PTH-CBD, which promote anagen phase transition of hair follicles, have been sought after due to their potential to treat a large variety of disorders of hair loss. PTH-CBD appears to have a similar mechanism of action to cyclosporine, which also promotes transition of hair follicles to anagen phase, although the mechanism is less likely to be the result of direct effects on WNT signaling. While clinical use of cyclosporine for this purpose is limited by systemic toxicity, PTH-CBD has not shown toxic effects, even with systemic administration.

Thus in another aspect, methods of increasing hair growth are provided herein. The methods include administering a CBD linked to a PTH/PTHrP receptor agonist to a subject in need of treatment to induce hair growth or stop hair loss. The method is applicable to individuals with alopecia, including chemotherapy induced alopecia, but also alopecia areata, alopecia caused by male pattern baldness, polycystic ovarian syndrome or other hair loss. The compositions may be administered locally or topically to treat hair loss.

In another aspect, methods of slowing hair growth or regrowth after a hair removal procedure by administering a CUD linked to a PTH/PTHrP receptor antagonist to a subject are provided. In one embodiment, the PTH antagonist composition is applied locally, topically. The PTH antagonist may be applied after a hair removal procedure to prevent or slow hair regrowth. As described in the Examples, we have demonstrated that hair regrowth is slowed after waxing in animals treated with CBD-PTH antagonist as compared to control animals treated with PTH CBD or vehicle alone. The compositions may be administered locally or topically to block hair growth.

Also provided herein are methods of treating hyperparathyroidism by administering PTH-CBD to a subject in need of treatment for hyperparathyroidism. In one embodiment the PTH administered to the subject may be a PTH from a different species. As shown in the Examples a single administration of CBD-PTH to ovarectomized aged rats was able to reduce the amount of endogenous PTH produced by the animal. Thus, administration of PTH-CBD to individuals suffering from hyperparathyroidism may experience a decrease in symptoms associated with hyperparathyroidism and have decreased levels of PTH after administration of PTH-CBD.

The collagen-binding polypeptide segment and the therapeutic agent may be chemically cross-linked to each other or may be polypeptide portions of a fusion protein. The terms "fusion protein" and "fusion polypeptide" may be used to refer to a single polypeptide comprising two functional segments, e.g., a collagen-binding polypeptide segment and a polypeptide based therapeutic agent, such as PTH/PTHrP receptor agonist polypeptide segment. The fusion proteins may be any size, and the single polypeptide of the fusion protein may exist in a multimeric form in its functional state, e.g. by cysteine disulfide connection of two monomers of the single polypeptide. A polypeptide segment may be a synthetic polypeptide or a naturally occurring polypeptide. Such polypeptides may be a portion of a polypeptide or may comprise one or more mutations. The two polypeptide segments of the fusion proteins can be linked directly or indirectly. For instance, the two segments may be linked directly through, e.g., a peptide bond or chemical cross-linking, or indirectly, through, e.g., a linker segment or linker polypeptide. The peptide linker may be any length and may include traditional or non-traditional amino acids. For example, the peptide linker may be 1-100 amino acids long, suitably it is 5, 10, 15, 20, 25 or more amino acids long such that the collagen binding portion of the fusion polypeptide can mediate collagen binding and the therapeutic agent can have its therapeutic effect. Peptide linkers may include but are not limited to a PKD (polycystic kidney disease) domain from a collagenase or other protein such as in SEQ ID NO: 2, a GST or His-tag, or a Ser or Gly linker.

The collagen-binding polypeptide segment is a polypeptide that binds collagen and may be part of a larger fusion protein, bioactive agent, or pharmaceutical agent. Determination of whether a composition, polypeptide segment, fusion protein, or pharmaceutical or bioactive agent binds collagen can be made as described in U.S. Patent Publication No. 2010/0129341, which is incorporated herein by reference in its entirety. Briefly, the composition is incubated with collagen in binding buffer, and the mixture is then filtered through a filter that would otherwise allow it to pass through but that blocks the collagen and therefore holds back materials that bind to the collagen. The filtrate is then assayed for the presence of the composition, polypeptide segment, fusion protein, or pharmaceutical or bioactive agent. Suitably, at least 80%, 85%, 90%, 95%, 98% or more suitably at least 99% of the collagen-binding composition, polypeptide segment, fusion protein, or pharmaceutical or bioactive agent is retained by the filter in this assay, as compared to when the filtration is performed without collagen.

The collagen-binding polypeptide segment may be a bacterial collagen-binding polypeptide segment. It may be a *Clostridium* collagen-binding polypeptide segment. The collagen-binding polypeptide segment may be a segment of a collagenase, or a bacterial collagenase, or a *Clostridium* collagenase. Suitably the polypeptide segment is only a portion of the collagenase and the collagen-binding polypeptide segment does not have collagenase activity. The collagen-binding polypeptide may be a bacterial M9B (including those derived from *Bacillus* spp. and *Clostridium* spp.) or M9A (including those derived from *Vibrio* spp.) collagen-binding protein or a collagen-binding peptide derived from such a protein. By "derived from" we mean that the peptide is a fragment of the full-length protein, a peptide that has amino acid changes relative to the wild-type protein or a combination thereof. The key is that the peptide retains the ability to bind collagen. For example, a peptide may be derived from a protein by selecting a region of the protein capable of binding to collagen. Compositions including a bacterial collagenase as a collagen binding peptide are described in US Patent Publication No. 2010/0129341, which is hereby incorporated herein by reference in its entirety.

Figure 1:
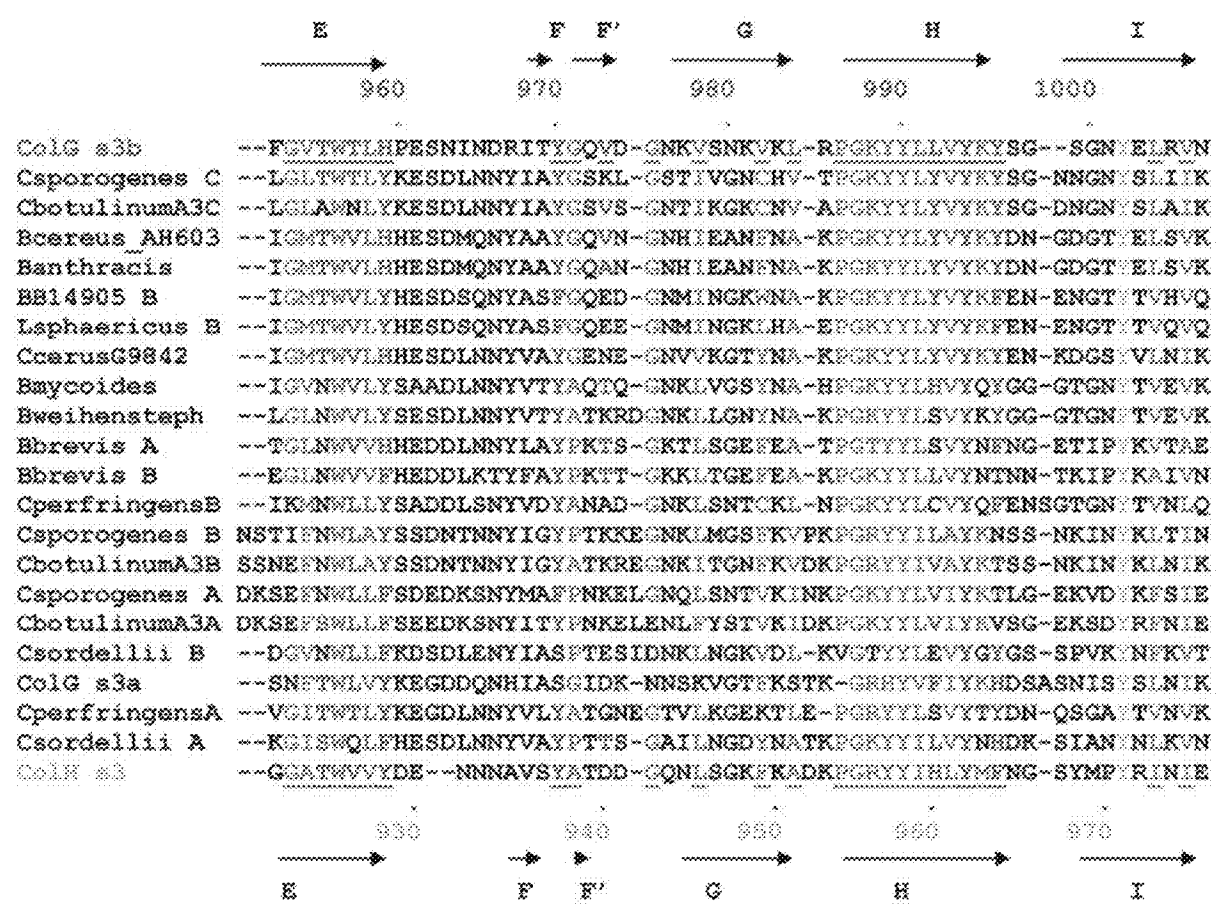

FIG. 1 shows a sequence alignment of the collagen-binding region of several M9B bacterial collagen-binding proteins included as SEQ ID NOs: 13-34. As can be seen from the sequence alignment, these proteins have a relatively small amount of sequence identity (about 30%), but they all bind to collagen in a similar fashion and are believed to have similar conformation as discussed in the Examples. Notably, the proteins share several amino acids critical for binding to collagen. Thus any of the peptides shown in FIG. 1 or collagen-binding fragments thereof can be used in the compositions and methods described herein (i.e., SEQ H) NOs: 13-34 can be used interchangeably).

In FIG. 1, the amino acid residues critical for the conformation of the peptide and for the collagen-binding activity are underlined and shown in green and blue respectively. The key amino acid residues for collagen-binding are as follows:

a phenylalanine, histidine or tyrosine at position 959 of ColG in FIG. 1 (position 63 of SEQ ID NO: 13), position 968 of the ColH sequence of SEQ ID NO: 6, position 928 of the ColH sequence of FIG. 1 (position 63 of SEQ ID NO: 34) or a similar position of one of the other sequences shown in FIG. 1;

a tyrosine, serine or phenylalanine at position 970 of ColG in FIG. 1 (position 74 of SEQ ID NO: 13), position 977 of the ColH sequence of SEQ ID NO: 6, position 937 of the ColH sequence of FIG. 1 (position 72 of SEQ ID NO: 34) or a similar position of one of the other sequences shown in FIG. 1;

a tyrosine at position 994 of ColG in FIG. 1 (position 98 of SEQ ID NO: 13), position 1002 of the ColH sequence of SEQ ID NO: 6, position 962 of the Corn sequence in FIG. 1 (position 97 of SEQ ID NO: 34) or a similar position of one of the other sequences shown in FIG. 1;

a tyrosine, phenylalanine or histidine at position 996 of ColG in FIG. 1 (position 100 of SEQ ID NO: 13), position 1004 of the ColH sequence of SEQ ID NO: 6, position 964 of the ColH sequence in FIG. 1 (position 99 of SEQ ID NO: 34) or a similar position of one of the other sequences shown in FIG. 1. The critical segment for collagen binding is amino acids 90-100 of SEQ ID NO: 13 which corresponds to amino acids 89-97 of SEQ ID NO: 34 or the equivalent thereof from another bacterial collagen binding protein such as the sequences provided in the alignment of FIG. 1 (SEQ ID NOs: 14-33). Thus a peptide with relatively low sequence identity, sharing the structure and function of the ColG protein may also be used as a collagen binding domain (CBD) herein.

In one embodiment, the collagenase is ColH, SEQ ID NO: 6. The collagen-binding polypeptide segment may be or may include residues 901-1021 of SEQ ID NO:6 (residues 34-158 of SEQ ID NO:1), or a fragment of residues 34-158 of SEQ ID NO:1 at least 8, 10, 12, 15, 20, 25, 30, 40, 50, 60, 70, 80, 90, 100, 110 or 120 amino acid residues in length. The collagen-binding polypeptide segment is at least 50%, 60%, 70%, 80%, or at least 85%, at least 90%, at least 95%, at least 96%, at least 98%, or at least 99% identical to residues 34-158 of SEQ ID NO: 1 or to any one of SEQ ID NO: 13-34. The collagen-binding polypeptide segment may be or may comprise a fragment of residues 901-1021 of SEQ NO:6, e.g., a fragment of at least 8, at least 10, at least 20, at least 30 at least 40, or at least 50 consecutive amino acid residues of residues 901-1021 of SEQ ID NO:6. Suitably the collagen-binding polypeptide consists of residues 894-1008, 894-1021, 901-1021, or 901-1008 of SEQ ID NO: 6 or a homolog thereof as shown by the sequence alignment in FIG. 1. As described more fully in the examples, the entire collagen binding polypeptides shown in FIG. 1 are not required for collagen binding. The collagen binding segment may be as short as eight amino acids and may include, e.g., amino acids 89-97 of SEQ ID NO: 34, 90-98 of SEQ ID NO: 13 or 994-1002 of SEQ ID NO: 6. A ten amino acid collagen binding peptide may include e.g., amino acids 89-99 SEQ ID NO: 34, 90-100 SEQ ID NO 13 or 994-1004 SEQ ID NO 6. A 30 amino acid collagen binding segment may include e.g., amino acids 70-100 of SEQ ID NOs: 13 or 34 or 975-1005 of SEQ ID NO: 6. A forty amino acid collagen binding peptide may include e.g, amino acids 60-100 of SEQ ID NOs: 13, 34 or 964-1004 of SEQ ID NO: 6, or 59-99 of SEQ ID NO: 34. A fifty amino acid collagen binding segment may include e.g., amino acids 50-100 or 55-105 of SEQ ID NOs:

13-34 or 9060-1010 of SEQ ID NO: 6. Similar shorter peptides derived for corresponding sequences of SEQ ID NOs: 14-33 may also be used.

The collagen-binding polypeptide segment may be or may include residues 807-1021 of SEQ ID NO: 6 (residues 37-251 of SEQ ID NO: 2), or a fragment of residues 807-1021 of SEQ ID NO:6 at least 8, 10, 12, 15, 20, 25, 30, 40, 50, 60, 70, 80, 90, 100, 110 or 120 amino acid residues in length. Residues 807-901 comprise the polycystic kidney disease (PKD) domain of the collagen-binding protein. Those of skill in the art will appreciate that other linkers could be used to link the collagen-binding peptide to a therapeutic agent as outlined above.

Among other proteins the collagen-binding segment can be derived from are ColG (Matsushita et al., (1999) J. Bacteria 181:923-933), a class I collagenase from *Clostridium histolyticum*. ColH is a class II collagenase (Yoshihara et al., (1994) J. Bacteriol. 176: 6489-6496). The collagen-binding polypeptide segment may also be a polypeptide segment from any one of the protein sequences provided in FIG. 1 which aligns collagen-binding peptides from members of *Clostridium* and *Bacillus*. Those of skill in the art will appreciate that other members of this collagen-binding protein family may be useful in the methods described herein.

The PTH/PTHrP receptor agonist polypeptide segment may be a synthetic polypeptide or a naturally occurring polypeptide. Such polypeptides may be a portion of a polypeptide or may comprise one or more mutations. The mutations may make the PTH/PTHrP receptor agonist a better or worse agonist as compared to the wild-type PTH/PTHrP. Agonist activity with the PTH/PTHrP receptor can be assayed as described in Example 3 below by a cAMP stimulation assay. An agonist will stimulate cAMP synthesis in the assay described. Suitably, an agonist can activate receptor activity at least 10%, 20%, 30%, 40%, 50%, 60%, 70%, 80%, 90%, 100% or oven 110% or 120% as much as wild-type PTH(1-34).

The PTH/PTHrP receptor agonist polypeptide segment is a PTH or PTHrP polypeptide segment. One human isoform of PTH is SEQ ID NO: 7. One human isoform of PTHrP is SEQ ID NO:8. While the human isoforms are provided, those of skill in the art will appreciate that other non-human-derived isoforms may be used as well. Such non-human-derived isoforms may be able to interact with human PTH/PTHrP receptor and vice versa. The PTH/PTHrP receptor agonist polypeptide segment may be or may include residues 1-33 of SEQ ID NO:1 (residues 1-33 of PTH (SEQ ID NO: 7)). The PTH/PTHrP receptor agonist polypeptide segment may be or may include residues 1-34 of PTH (SEQ ID NO: 7). In other embodiments, it is a fragment of residues 1-34 of PTH (SEQ ID NO: 7). In other embodiments, the PTH/PTHrP receptor agonist polypeptide segment may be or may include residues 1-84 of PTH (SEQ ID NO:7). In other embodiments, the PTH/PTHrP receptor agonist polypeptide segment may be or may include residues 1-14 of PTH (SEQ ID NO 7) or residues 1-7 of PTH (SEQ ID NO: 7). The key amino acids for binding to the PTH receptor ad an agonist are amino acids 1, 2 and 5 of PTH. In still other embodiments, the PTH/PTHrP receptor agonist is a PTH or PTHrP polypeptide segment for any other species.

The PTH/PTHrP receptor antagonist can include in one embodiment PTH(7-34), i.e., residues 7-34 of PTH (SEQ ID NO: 7). In another embodiment, it is or includes residues 7-33 of PIE (SEQ ID NO: 7). In other embodiments, it is a fragment of residues 7-34 of SEQ ID NO: 8. In another embodiment, the PTH/PTHrP receptor antagonist includes PIE (7-14), residues 7-14 of PTH (SEQ ID NO: 7). In another embodiment, the PTH/PTHrP receptor antagonists include ((−1)-33) of PTH/PTHrP. In another embodiment, the PTH/PTHrP receptor antagonists include residues 1-14 of PTH with an N-terminal extension. Adding an N-terminal extension to PTH or active N-terminal fragments of PTH converts the PTH peptides to antagonists. The N-terminal extension can be 1, 2, 3, 4, 5, or more amino acids in length. The identity of the amino acids in the N-terminal extension is typically not important. In one embodiment, the PTH/PTHrP receptor antagonist includes residues 1-33 of PTH with a Gly-Ser extension at the N-terminus (SEQ ID NO:11). In another embodiment, the PTH/PTHrP receptor antagonist includes PTHrP(7-34), i.e., residues 7-34 of SEQ ID NO:8, or a fragment of residues 7-34 of SEQ NO:8. In another embodiment, the PTH/PTHrP receptor antagonist includes mouse TIP(7-39) (See Hoare S R, Usdin T B. 2002. Specificity and stability of a new PTH1 receptor antagonist, mouse TIP(7-39). Peptides 23:989-98.). Other PTH/PTHrP receptor antagonists that may be used in the fusion proteins are also disclosed in Hoare et al. The PTH/PTHrP receptor antagonist may be a fragment of at least 8, 10, 12 or more amino acids from residues 1-34 of SEQ ID NO:7. In other embodiments the PTH/PTHrP receptor antagonist may be PTH/PTHrP receptor antagonist polypeptide from another species.

In one embodiment, the therapeutic agent or PTH/PTHrP receptor agonist or antagonist polypeptide segment is N terminal to the collagen-binding polypeptide segment in the fusion protein. That is, the two polypeptide segments each have an N-terminal and a C-terminal, and the N-terminal of the collagen-binding polypeptide segment is linked directly or indirectly, e.g., through a linker polypeptide segment (such as PKD, a Glycine or Serine linker) to the C-terminal of the therapeutic agent or PTH/PTHrP agonist or antagonist polypeptide segment.

The fusion proteins described above comprising (a) a collagen-binding polypeptide segment linked to (b) a therapeutic agent or a PTH/PTHrP receptor agonist or antagonist polypeptide segment can be replaced by pharmaceutical agents comprising (a) a collagen-binding polypeptide segment linked to (b) a therapeutic agent or PTH/PTHrP receptor agonist or a non-peptidyl PTH/PTHrP receptor agonist. An example of a non-peptidyl PTH/PTHrP receptor agonist is compound AH3960 (Rickard et al., (2007) Bone 39:1361-1372).

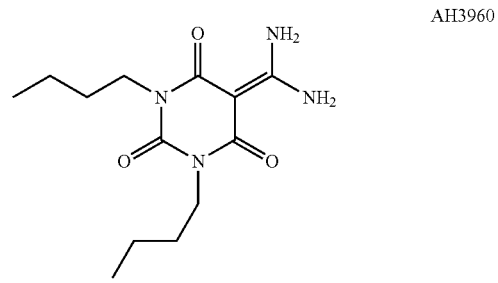 [SMILES: CCCCN1C(=O)C(=C(N)N)C(=O)N(CCCC)C1=O]

AH3960

AH13960 contains two amino groups. Amino groups in small chemical molecules such as AH3960 can be used to cross-link the therapeutic agent to amino groups on the collagen-binding polypeptide segment through a cross-linker such as DSG (disuccinimidyi glutarate) or through the combination of SANK (succinimidyl-4-hydrazinonicotinate acetone hydrazone) and SFB (succinimidyl-4-formyl benzoate). Therapeutic agents can be cross-linked through their amino group to a carboxyl group of the collagen-binding polypeptide segment by EDC (1-ethyl-3-[3-dimethylaminopropyl]carbodiimide hydrochloride) or vice versa. These cross-linking products are available from Pierce (piercenet.com, Thermo Fisher Scientific Inc., Rockford, Ill.). Protocols and reaction conditions are also available in the product literature from Pierce (piercenet.com).

In another embodiment of the pharmaceutical agents comprising (a) a collagen-binding polypeptide segment; linked to (b) a polypeptide therapeutic agent or a PTH/PTHrP receptor agonist or antagonist polypeptide segment, segment (a) and segment (b) are separate polypeptides, and the two polypeptides are linked by chemical cross-linking. The two polypeptides can be cross-linked through amino groups by reagents including DSG (disuccinimidyl glutarate) or glutaraldehyde. They can also be cross-linked through amino groups by derivatizing one polypeptide with SANH (succinimidyl-4-hydrazinonicotinate acetone hydrazone) and the other with SFB (succinimidyl-4-formyl benzoate), and then mixing the two derivatized polypeptides to cross-link. The two polypeptides can be cross-linked between an amino group of one polypeptide and a carboxyl of the other by reaction with EDC (1-ethyl-3-[3-dimethylaminopropyl]carbodiimide hydrochloride). The polypeptides can also be cross-linked (e.g., covalently coupled) by any other suitable method known to a person of ordinary skill in the art. These cross-linking reagents are available from Pierce (piercenet.com, Thermo Fisher Scientific Inc., Rockford, Ill.). Protocols and reaction conditions are also available in the product literature from Pierce (piercenet.com). These and other applicable cross-linking methods are described in U.S. published patent applications 2006/0258569 and 2007/0224119.

The compositions described herein may be administered by any means known to those skilled in the art, including, but not limited to, oral, topical, intranasal, intraperitoneal, parenteral, intravenous, intramuscular, intradermal or subcutaneous. Thus the compositions may be formulated as an ingestable, injectable, topical or suppository formulation. The composition may be formulated for administration by injection to result in systemic administration or local administration. The compositions may also be delivered with in a liposomal or time-release vehicle. The compositions may also be delivered in a site-directed delivery vehicle, such as but not limited to, a targeted liposome or an absorbable collagen sponge carrier or other implant.

The inventors have found that when administering compositions including a CBD subcutaneously it binds locally at the site of injection if the composition is dissolved in neutral pH buffer. But if the composition is dissolved in a low pH buffer, for example a buffer having pH 5.0 or pH 4.5 or below, the collagen-binding domain does not bind collagen, and the composition has time to disperse systemically before it binds collagen elsewhere in the body at neutral pH. Thus systemic administration of the compositions involves administering the composition dissolved in buffer or aqueous solution at a pH lower than about 5.0 or at pH 4.5 or below. In another embodiment, systemic administration of the compositions involves administering the fusion proteins dissolved in aqueous solution at lower than about 6.0. Alternatively, if the skin condition is localized, the compositions described herein may be administered in a buffer with a pH of 6.0, 6.5, 7.0, 7.5 or above in order to allow for localized delivery of the compositions to the affected area of the skin.

Pharmaceutical compositions for topical administration may also be formulated using methods and compositions such as those available to those skilled in the art. For example, gels, creams or liposome preparations may be suitable for topical delivery. These delivery vehicles may be formulated to mediate delivery to the lower layers of the skin or to allow for extended release of the pharmaceutical at the site of application.

The compositions can be administered as a single dose or as divided doses. For example, the composition may be administered two or more times separated by 4 hours, 6 hours, 8 hours, 12 hours, a day, two days, three days, four days, one week, two weeks, or by three or more weeks. Optionally, such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. The composition is expected to be more effective than a comparable or control composition comprising the therapeutic agent or a PTH/PTHrP receptor agonist that is not linked to a collagen-binding protein. In one embodiment, a smaller amount of the composition may be used or the composition may be administered less frequently than a comparable composition comprising the therapeutic agent or a PTH/PTHrP receptor agonist which is not linked to a collagen-binding protein.

The dosage amounts and frequencies of administration provided herein are encompassed by the terms therapeutically effective and prophylactically effective. The individual doses of pharmaceutical agents comprising a collagen-binding polypeptide segment linked to a therapeutic agent may be approximately the same on a molar basis as doses used for the therapeutic agent alone. It is expected that the pharmaceutical agents comprising a collagen-binding polypeptide segment linked to a therapeutic agent may be administered less frequently, because linking the agent to the collagen-binding polypeptide segment gives it much more prolonged activity in vivo.

Administration of the compositions to a subject in accordance with the invention appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the compositions being administered, the disease to be treated or inhibited, the condition of the subject, and other relevant medical factors that may modify the activity of the agent or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions of the invention and of the therapeutic agent administered alone, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the compositions will reduce symptoms of the condition being treated by at least 10%, 20%, 30%, 40%, 50%, 60%, 70%, 80%, 90% or 100% compared to pre-treatment symptoms or symptoms is left untreated. It is specifically contemplated that pharmaceutical preparations and compositions may palliate or alleviate symptoms of the disease without providing a cure, or, in some embodiments, may be used to cure the disease or disorder.

Suitable effective dosage amounts for administering the compositions may be determined by those of skill in the art, but typically range from about 1 microgram to about 10,000 micrograms per kilogram of body weight weekly, although they are typically about 1,000 micrograms or less per kilogram of body weight weekly. In some embodiments, the effective dosage amount ranges from about 10 to about 10,000 micrograms per kilogram of body weight weekly. In another embodiment, the effective dosage amount ranges from about 50 to about 5,000 micrograms per kilogram of body weight weekly. In another embodiment, the effective dosage amount ranges from about 75 to about 1,000 micrograms per kilogram of body weight weekly. The effective dosage amounts described herein refer to total amounts administered, that is, if more than one compound is administered, the effective dosage amounts correspond to the total amount administered.

The effectiveness of the compositions described herein may be enhanced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control treated with the therapeutic agent alone. It will be appreciated that the effectiveness of the treatment in any given case will be enhanced variably in accordance with the specific compositions used, the type of disease being treated, the condition of the subject, the specific formulations of the compounds and other relevant medical factors that may modify the activity of the compositions or the responses of the subject as is appreciated by those of skill in the art.

The following examples are meant only to be illustrative and are not meant as limitations on the scope of the invention or of the appended claims. All references cited herein are hereby incorporated by reference in their entireties.

EXAMPLES

Example 1

Structural Comparison of ColH and ColG Collagen-Binding Domains

The C-terminal collagen-binding domain (CBD) of collagenase is required for insoluble collagen fibril binding and for subsequent collagenolysis. The high resolution crystal structures of ColG-CBD (s3b) and ColH-CBD (s3) the molecules resemble one another closely (r.m.s.d. $C_\alpha$=1.5 Å), despite sharing only 30% sequence identity. Five out of six residues chelating $Ca^{2+}$ are conserved. The dual $Ca^{2+}$ binding sites in s3 are completed by a functionally equivalent aspartate. The three most critical residues for collagen interaction in s3b are conserved in s3. The general shape of the binding pocket is retained by altered loop structures and side-chain positions. Small angle X-ray scattering data revealed that s3 also binds asymmetrically to mini-collagen. Besides the calcium-binding sites and the collagen-binding pocket, architecturally important hydrophobic residues and hydrogen-bonding network around the cis-peptide bond are well-conserved in metallopeptidase subfamily M9B.

Common structural features described above and in Bauer et (2012) J Bacteriol November 9 (which is incorporated herein by reference in its entirety), enabled us to update the sequence alignment of the CBD in the M9B subfamily (FIG. 1). Conserved residues are important for one of four reasons: calcium chelation (red), cis-trans isomerization of the linker (yellow), collagen-binding (blue) or protein folding (green). FIG. 1 also indicates the strands of the structure along the top of the figure.

The dual calcium-binding site is formed by four chelating residues (Glu899, Glu901, Asn903, and Asp904) within the N-terminal linker, two chelating residues (Asp927 and Asp930) from the β-strand C and invariant Tyr1002 hydrogen-bonds and orients Asp930. Residue numbers used in this paragraph are of s3b. Likewise other supporting cast such as Gly921 is conserved in the middle of β-strand strategically placed to make room for Glu899. The dual calcium chelation site is fashioned sometimes by functionally equivalent residues. As mentioned, Asp897 of s3 acts equivalently to Asp927 of s3b. Asp897 equivalents are tentatively identified in *B. brevis* s3a and s3b, *C. botulinum* A3 s3a and *C. histolyticum* ColG s3a. Tridentate and divalent Asp and Glu residues are conserved with only *C. sordellii* s3a as the exception. The monodentate Asp904 residue is sometimes substituted by Asn. For those substituted, the net charge of the dual calcium site is neutral rather than −1.

The peptide between residues 901-902 has cis conformation in the holo state for both s3b and s3. The position 902 in other CBD molecules is Pro, Asp or Asn. Pro frequently succeeds the peptide bond to ease trans-cis isomerization. The s3 molecule has Pro. In s3b, OD of Asn902 hydrogen-bonds with the main-chain N of Asp904. The hydrogen-bond is critical for the peptide isomerization. Spiriti and van der Vaart. (2010) Biochemistry 49:5314-5320, which is incorporated herein by reference in its entirety. For the remainder of CBD molecules with Asp at the position, OD of Asp could play the same role as that of Asn902. Other hydrogen-bonds identified by simulation studies important in stabilizing the transition states are well conserved. These donor-acceptor pairs in s3 and s3b are tabulated (Table 1). Calcium ions could catalyze the isomerization in all the CBD molecules and their transition states and catalytic mechanism may look very similar.

TABLE 1

Hydrogen-bonds important in trans-cis peptide isomerization in s3b and their counterparts in s3.

| Important H-bonds in s3b for transition state formation | Corresponding H-bonds in s3 |
|---|---|
| T910_OG1 . . . N903_NH2 | S879_OG1 . . . N872_ND2 |
| T910_OG1 . . . N900_N | S879_OG1 . . . K86_N |
| E899_OE1 . . . N903_ND2 | E868_OE1 . . . N872_ND2 |
| E899_OE2 . . . S922_N | E868_OE2 . . . T891_N |
| N902_OD1 . . . D904_N | NA (N902 replaced with P871) |
| D930_OD2 . . . Y1002_OH | D939_OD2 . . . Y97_OH |
| Y1002_OH . . . Y932_OH | NA (Y932 replaced with F901) |

Non-functional residues that are important in either folding or architectural stability are conserved. Hydrophobic residues packed between the β-sheets are better conserved if they are located in the vicinity of functionally critical residues. For example, invariant Trp956 of strand E is packed between the β-sheets. The residues flanking (Thr955

& Thr957) interact with mini-collagen. Tyr932 is packed between the sheets and helps positioning Tyr1002. Residues at tight turns are conserved as well. Gly975 is well conserved to allow a type II' turn in s3b, Gly942 (Gly975 equivalent) in s3 allows Asp941 side-chain to stabilize the reverse turn. A highly conserved six-residue stretch, between residues 986 and 991, adopts a tight turn and precedes the functionally important strand H. The region is well ordered in the crystal structures with low B-factors, and is the least dynamic based on NMR and limited proteolysis MALDI-TOF MS. Philominathan, et al. (2009) J Biol Chem 284: 10868-10876 and Sides et al. J Am Soc Mass Spectrom. (2012) 23(3):505-19 both of which are incorporated herein by reference in their entireties. The main-chain carbonyl and amino groups of Arg985 hydrogen-bond with OH of Tyr989 to stabilize the turn. Only Gly987 can make room for the bulky Tyr989 side chain. Try990 packs against the invariant Ala909 and conserved $3_{10}$ helix. Ala909 is at the base of the linker that undergoes α-helix→β-strand transformation. The tight turn may ensure that collagen interacting Leu992, Tyr994, and Tyr996 would be correctly positioned. Tyr994 is the most critical residue in interacting with collagenous peptides. Wilson, et al. (2003) EMBO J. 22:1743-1752. The strands adjacent to strand H, i.e. strands C and E, are very well conserved. The three antiparallel strands mold the collagen-binding pocket. Strand F staples the β-sheets by interacting with both sheets. The β-strand first interacts in an antiparallel orientation with strand E then breaks its direction at Gly971 to interact with strand G. In place of Gly971, Ala or Pro is found at the location where the strand switches its allegiance. The dual interaction of the strand helps positioning Tyr970 to interact with mini-collagen.

Three residues shown to interact strongly with mini-collagen are conserved. The invariant Tyr994 and well conserved Tyr970 and Tyr996 constitute the "hot spot". Y994A mutation lost binding capability. Since Y994F resulted in 12-fold reduction in binding to mini-collagen, the hydroxyl group of Tyr994 may interact with collagen through a hydrogen-bond. Tyr996, which is a critical residue in binding mini-collagen, is not so well conserved. Y996A caused 40-fold reduction in binding to the mini-collagen. Y996 is s3b is replaced with Phe in s3, though both side chains have identical orientation. In other CBD molecules, an aromatic residue, such as Phe or His, is sometimes found at the site. Y970A results in 12-fold reduction in binding to mini-collagen. Thr957 was found to interact with mini-collagen by $^{15}$N-HSQC-NMR titration. The β-branched amino acid residues or Leu are found at the positions equivalent to Thr957 in most of the CBDs. Six other residues were identified by $^{15}$N-HSQC-NMR titration to interact with mini-collagen are not very well conserved. Since divergent CBDs (s3 and s3b) adopted a similar saddle-shaped binding pocket, other CBDs may also adopt similar collagen-binding strategy.

Divergent CBD could target different collagen sequences and could possibly target different collagen types; however, this structural study suggest otherwise. Rather, all the CBD domains may bind similarly to an under-twisted region such as the C-terminus of a collagen fibril. The C-terminus of type I collagen is exposed in the fibril surface based on X-ray fiber diffraction experiments, and it is the most accessible site for the bacterial collagenase to initiate assaults. However CBD binding only at the C-terminal region of tropocollagen is unfounded. Gold particle-labeled tandem ColG-CBD (s3a-s3b) labeled with gold particle bound to type I collagen fibrils exhibited no periodicity. In the collagen fibrils, the molecules are staggered from each other by about 67 nm. Therefore CBD could target partially under-twisted regions in the middle of a tropocollagen that are also vulnerable for assaults.

Much like s3b, s3 is both compact, and extremely stable in the presence of physiological $Ca^{2+}$. Thus, the enzyme could degrade extracellular matrix for prolonged time. The linker that induced structural transformation is a common feature found in M9B collagenase. It could act as $Ca^{2+}$ to trigger domain rearrangement as means of enzyme activation. $Ca^{2+}$ concentration in extracellular matrix is higher than that inside a bacterium. Both s3 and s3b bind similarly to a mini-collagen, thus M9B collagenase molecules could initiate collagenolysis from analogous structural features in various collagen fibril. Fusion protein of any CBD derived from M9B collagenase and a growth factor should result in comparable clinical outcome.

Example 2

CBD-PTH Agonist Spurs Hair Growth and CBD-PTH Antagonist Inhibits Hair Growth

In-Vitro Characterization of CBD-Linked PTH Compounds:

Collagen binding of each peptide was verified in flow-through collagen binding assays as previously described in U.S. Patent Publication No. 2010/0129341, which is incorporated herein by reference in its entirety. PTH-CBD, consisting of the first 33 amino acids of PTH linked directly to the collagen binding domain (SEQ ID NO 1), was the most potent agonist, having a similar effect to that of PTH(1-34) (SEQ ID NO: 7) on cAMP accumulation. Ponnapakkam et al. (2011) Calcif 88:511-520. Epub 2011 April 2022. Among the antagonists, PTH(7-33)-CBD (SEQ ID NO: 10) had the best combination of low intrinsic activity and high receptor blockade (not shown), similar to those seen in other PTH antagonists, including those used in hair growth studies. Peters, et al. (2001) J Invest Dermatol 117:173-178.

In Vivo Distribution of PTH-CBD:

Tissue distribution was assessed by administering $^{35}$S-labelled PTH-CBD via subcutaneous injection, followed by whole mount frozen and whole-body autoradiography. PTH-CBD with a phosphorylation site between PTH(1-33) and the CBD was purified, activated and labeled with [gamma-35] ATP as described previously. Tamai et al. (2003) Infect Immun. 71:5371-5375. Approximately 10.8 meg of $^{35}$S-PTH-CBD (122 kcm/mcg) was injected subcutaneously in 7 week-old mice (32-35 g). Mice were sacrificed at 1 hour or 12 hours post-injection, and then frozen in dry ice-acetone. Frozen sections (50 μm) were prepared with an autocryotome, dried at −20° C., and exposed to an image plate for 4 weeks. There appeared to be an initial distribution of $^{35}$S-PTH-CBD to a broad area of skin around the site of injection, followed by a rapid redistribution to the skin of the entire animal, as well as to several other tissues (i.e. bone, intestine, bladder) (FIG. 2). PTH-CBD thus showed the desired properties of distribution and retention to skin with subcutaneous administration.

PTH-CBD Reverses Hair Loss in Chemotherapy-Induced Alopecia in Mice:

We compared efficacy of CBD linked PTH agonists and antagonists in chemotherapy-induced alopecia, utilizing an experimental design published by Peters, et al., for non-CBD linked PTH compounds. Peters, et al. (2001) J Invest Dermatol 117:173-178. C57BL/6J mice (Jackson Laboratories, Bar Harbor, Me.) were depilated to synchronize the hair follicles, and cyclophosphamide (CYP, 150 mg/kg) was administered on day 9 to maximize the chemotherapy-induced damage. The agonist (PTH-CBD) and the antagonist (PTH(7-33)-CBD) were administered 2 days prior to chemotherapy, and given the long-term retention of the compounds in the skin, we administered only a single dose to cover the timing of the multiple injections of PTH agonist and antagonist in the study by Peters, et. al. The administered dose of CBD-linked compounds (320 meg/kg) is well tolerated in mice. Ponnapakkam et al. (2011) Calcif 88511-520. Epub 2011 April 2022.

Figure 3:
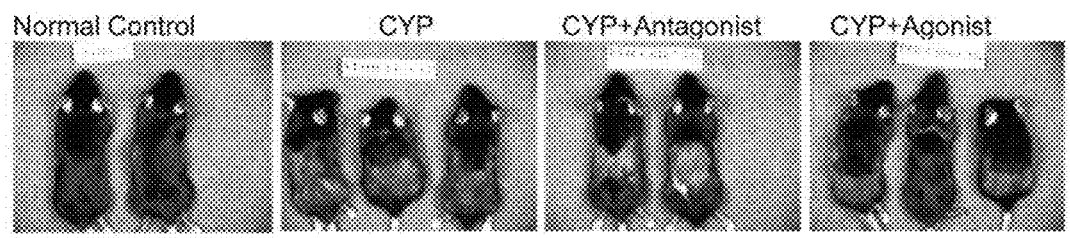
FIG. 3 is a set of photographs documenting the hair growth on the back of mice at day 36 after depilation, treatment groups as indicated (Antagonist PTH(7-33)-CBD, Agonist PTH-CBD).
Figure 4:
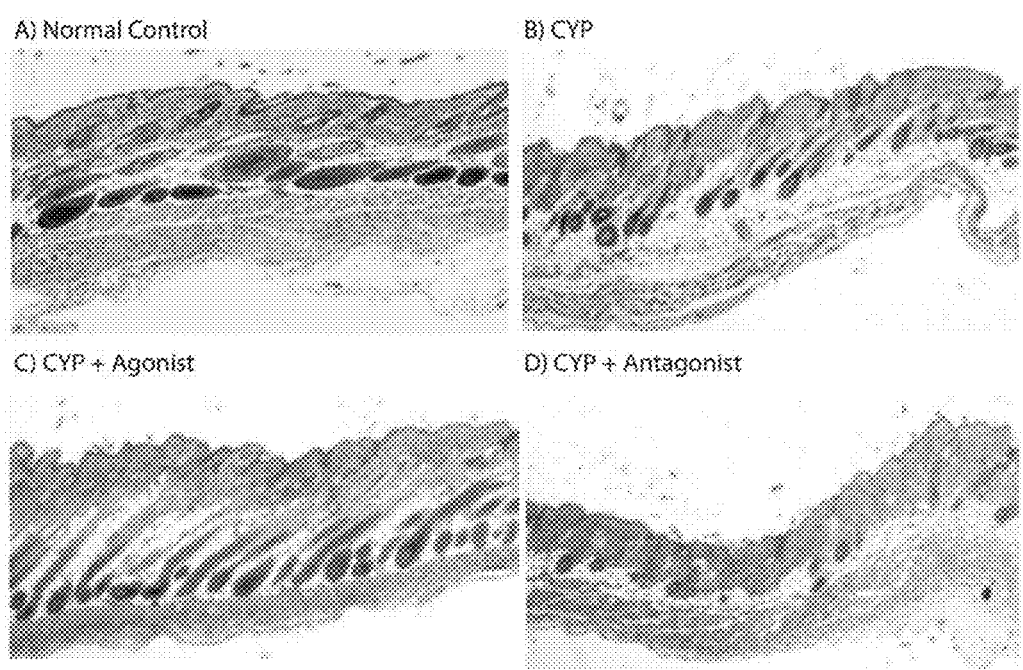
FIG. 4 is a set of photographs showing the histology at Day 36 after the indicated treatment. Skin samples were taken from the dorsal region and processed for Hematoxylin and Eosin (H&E) staining. Representative sections are shown from each treatment group as indicated. (Antagonist=PTH(7-33)-CBD, Agonist=PTH-CBD).
Figure 5:
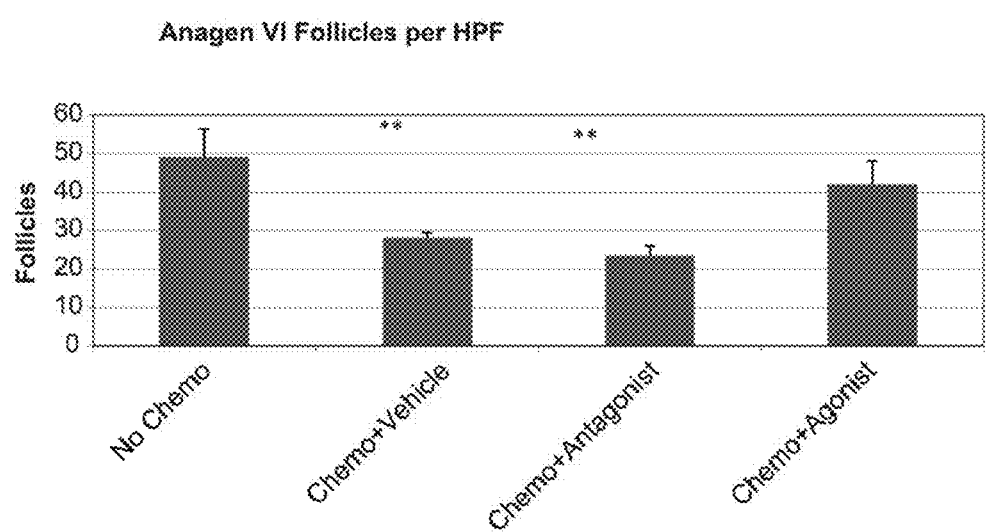
FIG. 5 is a graph showing the hair follicle counts per high powered field. Anagen VI hair follicles were counted by two independent observers in a blinded fashion. Results are expressed as mean+/−standard deviation. **=p<0.01 vs. no chemo ANOVA followed by Dunnett's test. (Antagonist=PTH(7-33)-CBD, Agonist PTH-CBD).

The results of the photodocumentation record indicate that the agonist, PTH-CBD, was far more effective at stimulating hair growth than was the antagonist (FIG. 3). Histological examination revealed morphological changes in the hair follicles after CYP therapy, which were more superficially located and exhibited clumped melanocytes around the bulb, characteristics of the dystrophic anagen and catagen phase (FIG. 4). While the antagonist PTH(7-33)-CBD had no beneficial effect, treatment with the agonist PTH-CBD led to deeper rooting and reduced melanocyte clumping, thus reversing the dystrophic changes. Counts of anagen VI hair follicles per high-powered field (HPF) were compared between groups; animals treated with PTH-CBD had a higher number of hair follicles, approaching those of animals which did not receive chemotherapy (FIG. 5), while the antagonist PTH(7-33)-CBD had no beneficial effect.

Importantly, we saw no evidence of adverse effects from PTH-CBD administration. While PTH injections are known to elevate blood calcium and can cause kidney stones, PTH-CBD had no effect on serum calcium. In addition, there was no evidence of excess hair length on the body or of excess hair growth on the ears and tail, where a full coat is normally not present. The effects of PTH-CBD on hair growth have been confirmed in models of chemotherapy-induced alopecia without depilation, which more closely mimic clinical protocols.

Figure 6:
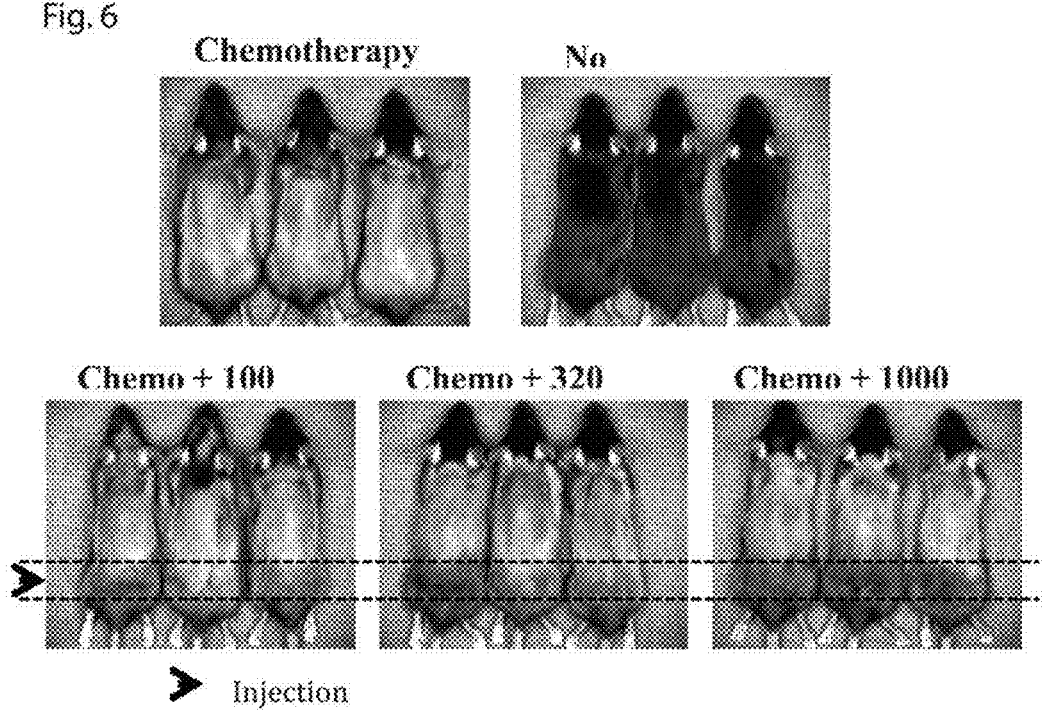
FIG. 6 is a set of photographs showing the hair growth on the back of the mice after each of the indicated treatments and a graph showing the results of a grey scale analysis of the hair at the injection site over time after the injection.
Figure 6:
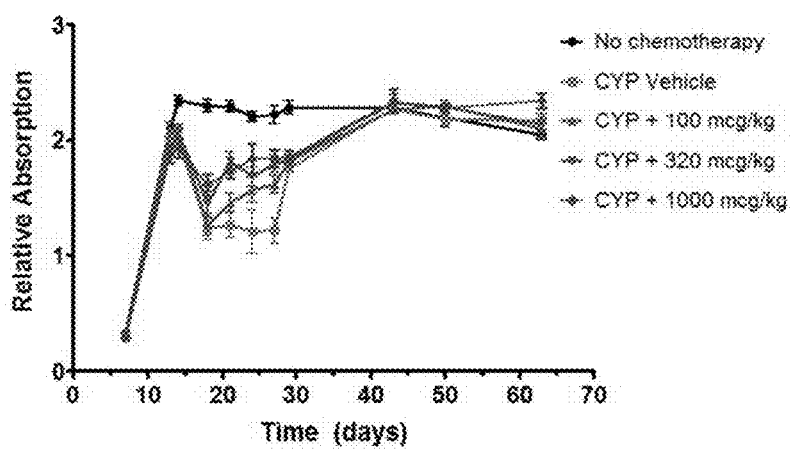

Quantification of Effects of PTH-CBD in Chemotherapy-Induced Alopecia:

We followed these studies by comparing the effects of different doses of PTH-CBD in chemotherapy-induced alopecia. In these studies, we applied the injections more distally on the back and applied a gray-scale analysis to quantify the amount of hair growth. Injecting more distally in the back allows us to compare regrowth of hair after PTH-CBD treatment with less interference from the normal hair regrowth, which normally proceeds from head to tail in mice. The results are shown in FIG. 6, indicating a dose-dependent effect on hair regrowth both qualitatively and quantitatively.

Figure 7:
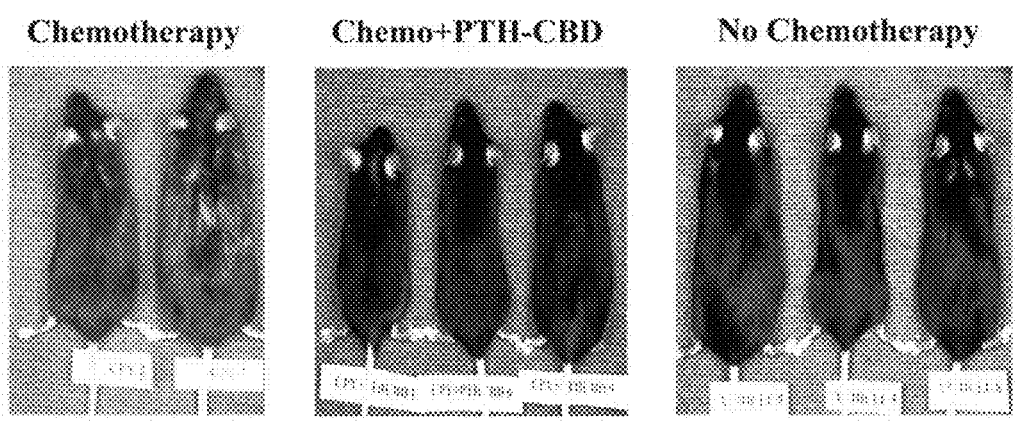
FIG. 7 is a set of photographs showing the hair on the back of mice after the indicated treatment without prior depilation.

Chemotherapy-Induced Alopecia without Depilation:

While the depilated model of chemotherapy-induced alopecia provides a uniform model for comparison of drug effects, the depilation process is known to cause hair follicle injury, and may alter the response of the animals to the PTH-CBD administration. We therefore tested the effects of PTH-CBD in another model of chemotherapy-induced alopecia, where the animals were given 3 courses of cyclophosphamide therapy (50 mg/kg/wk), similar to the usual manner in which cancer patients might be treated. In this model, it takes much longer (4-6 months) for alopecia to develop. Animals that received a single dose of PTH-CBD (320 meg/kg subcutaneous) prior to the first cycle did not develop hair loss as shown in FIG. 7.

Figure 8:
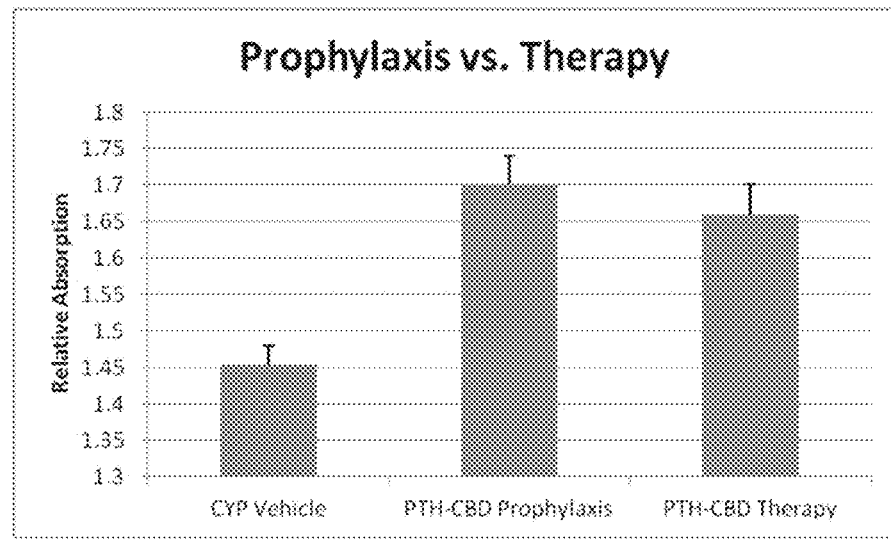
FIG. 8 is a set of photographs and a graph showing the grey scale analysis of hair growth on the backs of mice comparing the indicated treatments with the PTH-CBD being administered prior to the chemotherapy as opposed to after chemotherapy began.
Figure 8:
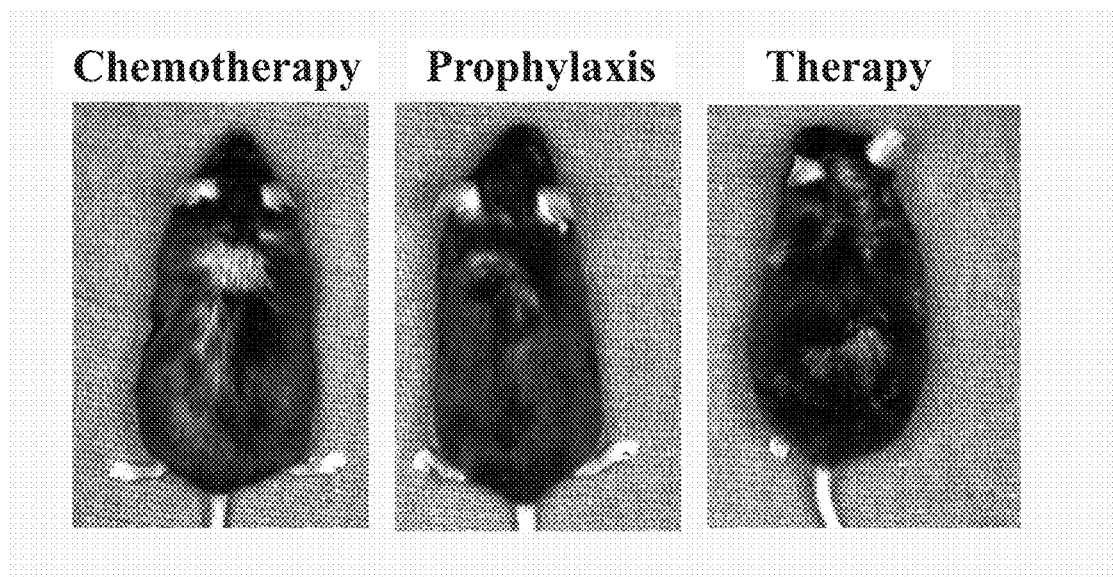

In a second study, we compared the effects of PTH-CBD when given prophylactically, at the time of the first cycle of chemotherapy, vs. therapeutically, after the hair loss had developed. While PTH-CBD was effective in both instances, the effects were more prominent when given prophylactically. This is evident both visually and quantitatively in FIG. 8, using the same grey scale analysis used in our dose-response study.

Figure 9:
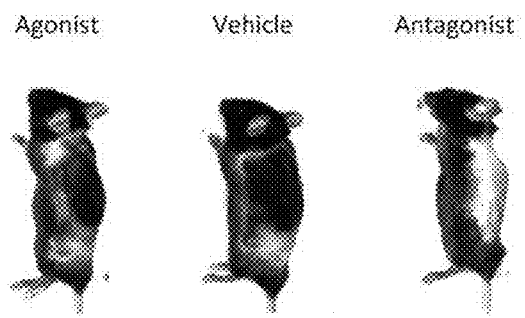
FIG. 9 is a photograph of three mice 13 days after waxing to remove hair and treatment with PTH-CBD, PTH antagonist-CBD or vehicle alone.

Depilation Alopecia:

The agonist PTH-CBD appears to increase hair growth by increasing the number of anagen phase hair follicles. As such, there is no reason to believe that hair growth effects should be limited to the chemotherapy model. We therefore tested both PTH-CBD and antagonist compound, PTH(7-33)-CBD, after removing hair from C57/BL6J mice by waxing (FIG. 9). The results were quite interesting; agonist (PTH-CBD) treated animals had earlier anagen eruption (day 7 vs. day 9 for vehicle controls), and exhibited more complete regrowth of hair by the end of the study (day 18). Antagonist (PTH(7-33)-CBD) treated animals also had an early anagen eruption, but the hair growth which followed was markedly curtailed, and the hair cycle was arrested after this point, resulting no further observed regrowth of hair. Thus, it appears that agonist therapy is acting to promote more rapid regrowth of hair by promoting more rapid transition to the anagen phase, while the antagonist inhibited hair regrowth by blocking this transition.

PTH-CBD is a fusion protein of the first 33 amino acids of parathyroid hormone (PTH) and a bacterial collagen binding domain. The collagen binding activity causes PTH-CBD to be retained at its site of action in the dermal collagen, maximizing efficacy and reducing systemic side-effects. PTH-CBD stimulates hair growth by causing hair follicles to enter an anagen VI or growth phase, presumably by activating WNT signaling and increasing production of beta-catenin. We therefore plan to conduct the following additional studies to confirm this mechanism of action and to determine the effect of PTH-CBD in two distinct genetic mouse models with WNT signaling inhibition. These data will be used in formulating clinical trials for PTH-CBD as a therapy for alopecia.

Figure 10:
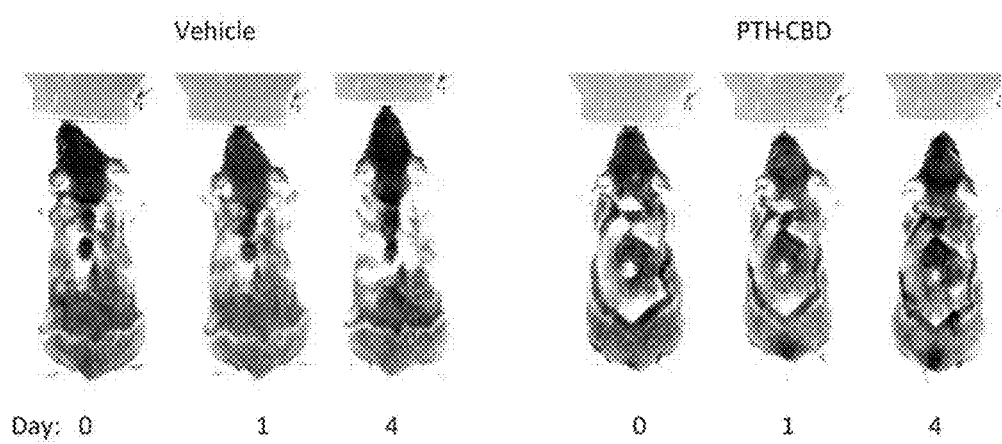
FIG. 10 is a set of photographs of mice showing hair regrowth in a model of alopecia areata after treatment with a control or with PTH-CBD.

Alopecia Areata Alopecia:

Areata is a disease of patchy hair loss due to autoimmune destruction of the hair follicles. We tested the efficacy of PTH-CBD in promoting regrowth of hair in an animal model of alopecia areata, the engrafted C3H/Hej mouse. In this model, hair loss develops variably over the first 2 months of life. Shown in FIG. 10 is the results of a single dose of PTH-CBD (320 meg/kg subcutaneous) administered into the engrafted site, the center of the back, where there was maximal hair loss. Compared to vehicle control animals, which continued to lose hair at this site, animals receiving PTH-CBD began to show regrowth of hair within the next 1-4 days. Importantly, the response was found to be sustained during the 2 month course of the experiment.

Example 3

CBD-PTH can Prevent or Treat Hyperparathyroidism

Figure 11:
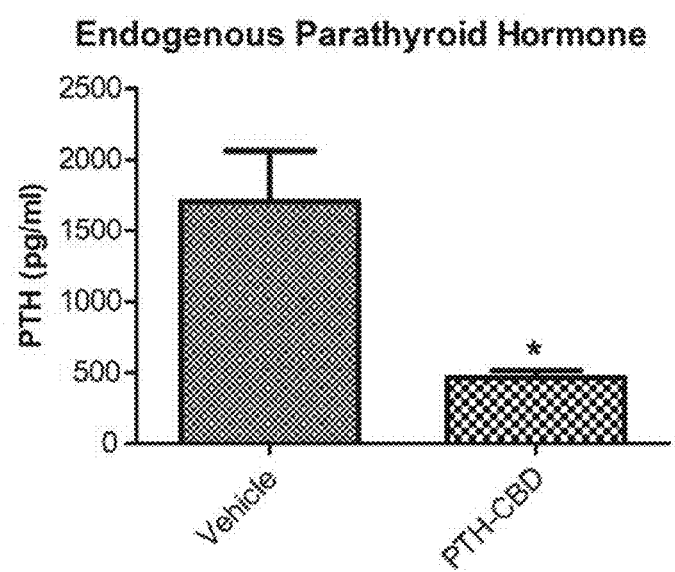
FIG. 11 is a graph showing the endogenous parathyroid hormone levels in ovarectomized aged rats injected with a single dose of human PTH-CBD 6 months prior to sacrifice.

In this experiment, rats had their ovaries surgically removed at age 3 months. At age 9 months, rats were injected with either a single dose of PTH-CBD (320 mcg/kg) or vehicle control. Animals were sacrificed 6 months after therapy (age 15 months). Human intact PTH levels were measured to assess serum levels of PTH-CBD, and were found to be undetectable in both groups. Serum calcium was measured and there were no differences between groups (Vehicle: 13.5+/−1.1 vs. PTH-CBD: 14.3+/−1.1 mg/dl, NS). Rat intact PTH levels were measured to assess endogenous PTH production, and PTH-CBD suppressed the normal increase in endogenous PTH levels seen in aged, ovarectomized rats (FIG. 11). These findings indicate that a single injection of PTH-CBD can provide long-term suppression of endogenous PTH production, preventing the normal rise seen with age in the ovarectomized rat model, and thus may serve as a therapy for hyperparathyroidism.

We claim:

1. A method of slowing hair growth comprising administering a composition comprising a bacterial collagen-binding polypeptide segment linked to a PTH/PTHrP receptor antagonist to a subject to slow hair growth relative to the hair growth the subject would experience without treatment, wherein the bacterial collagen-binding polypeptide segment comprises a collagen-binding polypeptide derived from an M9 peptidase selected from the group consisting of, one of SEQ ID NOs: 13-34 or a fragment of at least 8 consecutive amino acids of SEQ ID NOs: 13-34, residues 34-158 of SEQ ID NO: 1, a fragment of at least 8 consecutive amino acids from residues 34-158 of SEQ ID NO: 1, and a peptide that is at least 90% identical to residues 34-158 of SEQ ID NO: 1 or SEQ ID NOs: 13-34, and wherein the PTH/PTHrP receptor antagonist comprises a sequence selected from the group consisting of residues 7-33 of SEQ ID NO: 7, residues 7-14 of SEQ ID NO: 7, a fragment of at least 8 consecutive amino acids from residues 7-34 of SEQ ID NO: 7, and residues ((−1)-33) of PTH.

2. The method of claim 1, wherein the composition is administered locally.

3. The method of claim 2, wherein the composition is administered topically.

4. The method of claim 1, wherein and the N-terminus of the collagen-binding polypeptide segment is linked directly or through a linker polypeptide segment to the C-terminus of the PTH/PTHrP receptor antagonist polypeptide.

5. The method of claim 1, wherein the collagen-binding polypeptide segment and the PTH/PTHrP receptor antagonist polypeptide are chemically cross-linked to each other or are polypeptide portions of a fusion protein.

6. The method of claim 1, wherein the subject is human.

7. The method of claim 1, wherein the bacterial collagen-binding polypeptide segment comprises residues 34-158 of SEQ ID NO: 1 or a peptide that is at 90% identical to residues 34-158 of SEQ ID NO: 1.

8. The method of claim 1, wherein the PTH/PTHrP receptor antagonist comprises residues 7-33 of SEQ ID NO: 7.

9. The method of claim 1, wherein the bacterial collagen-binding polypeptide segment linked to the PTH/PTHrP receptor antagonist is a fusion protein comprising SEQ ID NO: 10.

10. The method of claim 4, wherein the linker polypeptide segment comprises a PKD domain.

11. The method of claim 10, wherein the PKD domain comprises residues 807-901 of SEQ ID NO: 6.

12. The method of claim 1, wherein the composition is administered after the subject undergoes a hair removal procedure.

* * * * *

UNITED STATES PATENT AND TRADEMARK OFFICE
CERTIFICATE OF CORRECTION

PATENT NO. : 9,526,765 B2
APPLICATION NO. : 14/378067
DATED : December 27, 2016
INVENTOR(S) : Tulasi Ponnapakkam et al.

Page 1 of 1

It is certified that error appears in the above-identified patent and that said Letters Patent is hereby corrected as shown below:

In the Specification

Column 1, replace the paragraph Lines 17-22, with the following:
This invention was made with government support under Grant Numbers P20 RR015569 and P20 RR016460 awarded by the National Institutes of Health. The government has certain rights in this invention.

Signed and Sealed this
Second Day of June, 2020

Andrei Iancu
*Director of the United States Patent and Trademark Office*